(12) United States Patent
Pawliszyn

(10) Patent No.: US 7,384,794 B2
(45) Date of Patent: Jun. 10, 2008

(54) MICRO-DEVICES AND ANALYTICAL PROCEDURES FOR INVESTIGATION OF BIOLOGICAL SYSTEMS

(76) Inventor: Janusz B. Pawliszyn, 383 Dunvegan Drive, Waterloo, Ontario (CA) N2K 1W7

(*) Notice: Subject to any disclaimer, the term of this patent is extended or adjusted under 35 U.S.C. 154(b) by 0 days.

(21) Appl. No.: 10/506,827

(22) PCT Filed: Mar. 6, 2003

(86) PCT No.: PCT/CA03/00311

§ 371 (c)(1),
(2), (4) Date: Sep. 7, 2004

(87) PCT Pub. No.: WO03/075772

PCT Pub. Date: Sep. 18, 2003

(65) Prior Publication Data

US 2005/0118599 A1    Jun. 2, 2005

Related U.S. Application Data

(60) Provisional application No. 60/427,833, filed on Nov. 21, 2002, provisional application No. 60/421,510, filed on Oct. 28, 2002, provisional application No. 60/421,001, filed on Oct. 25, 2002, provisional application No. 60/393,309, filed on Jul. 3, 2002, provisional application No. 60/364,214, filed on Mar. 11, 2002.

(51) Int. Cl.
| | |
|---|---|
| *G01N 1/18* | (2006.01) |
| *G01N 33/567* | (2006.01) |
| *G01N 21/00* | (2006.01) |
| *C12M 1/34* | (2006.01) |
| *A01N 1/00* | (2006.01) |
| *B01L 9/00* | (2006.01) |
| *B32B 5/02* | (2006.01) |
| *A61K 49/00* | (2006.01) |
| *A61B 5/055* | (2006.01) |
| *A61B 1/00* | (2006.01) |
| *A61B 5/00* | (2006.01) |
| *A61L 33/00* | (2006.01) |

(52) U.S. Cl. ............ 436/178; 436/807; 435/287.1; 435/287.2; 435/7.21; 435/284.1; 422/104; 422/119; 422/57; 422/58; 424/9.1; 424/9.34; 427/2.1; 427/2.11; 427/2.12; 427/2.13; 427/8; 427/180; 427/181; 600/114; 600/308; 600/325; 600/326; 600/327; 600/341; 600/368; 600/585

(58) Field of Classification Search ............ 436/178, 436/807; 435/7.21, 284.1, 287.1, 2; 422/57, 422/58, 104, 119; 424/9.1, 9.34; 427/2.1–2.13, 427/8, 180–181; 600/114, 308, 325–327, 600/341, 368, 585

See application file for complete search history.

(56) References Cited

U.S. PATENT DOCUMENTS 4,616,652 A * 10/1986 Simpson ............ 606/194

(Continued)

OTHER PUBLICATIONS

Moneti et al., "Solid-phase Microextraction of Insect Epicuticular Hydrocarbons for Gas Chromatographic/Mass Spectrometric Analysis", Rapid Communications in Mass Spectrometry, vol. II, 1997 pp. 857-862.

(Continued)

*Primary Examiner*—Long V. Le
*Assistant Examiner*—Jacqueline DiRamio
(74) *Attorney, Agent, or Firm*—Andrew D. Sojonky; Borden Ladner Gervais LLP

(57) ABSTRACT

Fibres with an extraction phase coated thereon in combination with a positioning device are described to perform adsorption of components of interest from an animal or animal tissue for the investigation of living systems. A number of interfaces to analytical instrumentation are disclosed including mass spectrometry, LC/MS, MALDI and CE as well as direct spectroscopic on-fibre measurement.

23 Claims, 27 Drawing Sheets

U.S. PATENT DOCUMENTS

| | | | |
|---|---|---|---|
| 5,120,510 A * | 6/1992 | Gourley et al. | 422/82.07 |
| 5,424,187 A * | 6/1995 | Shor et al. | 435/6 |
| 5,464,395 A * | 11/1995 | Faxon et al. | 604/103.02 |
| 5,640,470 A * | 6/1997 | Iyer et al. | 385/12 |
| 5,691,206 A * | 11/1997 | Pawliszyn | 436/178 |
| 6,287,521 B1 * | 9/2001 | Quay et al. | 422/101 |
| 6,689,603 B2 * | 2/2004 | Pompidou et al. | 435/287.2 |
| 6,730,096 B2 * | 5/2004 | Basta | 606/108 |
| 6,743,180 B1 * | 6/2004 | Van Bockel | 600/505 |
| 2002/0034827 A1 | 3/2002 | Singh et al. | |
| 2003/0135195 A1* | 7/2003 | Jimenez et al. | 604/500 |
| 2003/0180954 A1* | 9/2003 | Riviere et al. | 436/5 |
| 2003/0183758 A1* | 10/2003 | Colburn et al. | 250/287 |
| 2004/0171169 A1 | 9/2004 | Kallury et al. | |
| 2005/0032237 A1 | 2/2005 | Sandra et al. | |
| 2005/0142033 A1 | 6/2005 | Glezer et al. | |

OTHER PUBLICATIONS

Frérot et al., "Solid-Phase Microextraction (SPME): A New Tool in Pheromone Identification in Lepidoptera", J. High Resolut. Chromatogr., 1997, 20, pp. 340-342.

Smith et al., "Solid-Phase Microextraction as a Tool For Studying Volatile Compounds in Frog Skin", Chemistry and Ecology, 2000, vol. 17, pp. 215-225.

Heinze, "Ultramicroelectrodes in Electrochemistry", Angew. Chem. Int. Ed. Engl., 1993, 32, pp. 1268-1288.

Whang et al., "Solid phase microextraction coupled to capillary electrophoresis", J. Anal. Commun., 1998, 35, pp. 353-356.

Jackson et al., "Mass spectrometry for genotyping: an emerging tool for molecular medicine", Molecular Medicine Today, Jul. 2000, vol. 6, pp. 271-276.

Namera et al., "Analysis of anatoxin-a in aqueous samples of solid-phase microextraction coupled to high-performance liquid chromatography with fluorescence detection and on-fiber derivatization", *Journal of ChromatographyA*, 963, Jul. 19, 2002, pp. 295-302.

* cited by examiner

MICRO-DEVICES AND ANALYTICAL PROCEDURES FOR INVESTIGATION OF BIOLOGICAL SYSTEMS

This application is entitled to the benefit of and claims priority to U.S. patent application Ser. No. 60/364,214 filed Mar. 11, 2002; U.S. patent application Ser. No. 60/393,309 filed Jul. 3, 2002; U.S. patent application Ser. No. 60/421,001, filed Oct. 25, 2002; U.S. patent application 60/421,510 filed Oct. 28, 2002; and U.S. patent application Ser. No. 60/427,833 filed Nov. 21, 2002, the entirety of each document being incorporated herein by reference.

FIELD OF THE INVENTION

The present invention relates generally to devices and methods for quantifying or identifying components of interest in a biological system, such as in an animal.

BACKGROUND OF THE INVENTION

Presently, if one wants to accurately assess the concentrations of chemicals or drugs inside a living animal a sample of the blood or tissue to be studied is removed from the animal and taken to an analytical laboratory to have the chemicals of interest extracted and quantified. Typically a first step is a pre-treatment of the sample to convert it to a form more suitable for chemical extraction. In the case of blood this may be by the removal of blood cells and/or some blood components by the preparation of serum or plasma. In the case of a tissue sample this may be by many processes including freezing, grinding, homogenizing, enzyme treatment (eg. protease or cellulase) or hydrolysis. Subsequently chemicals of interest are extracted and concentrated from the processed sample. For example serum samples may be subjected to liquid-liquid extraction, solid phase extraction or protein precipitation followed by drying and reconstitution in an injection solvent. A portion of the injection solvent is introduced to an analytical instrument for chromatographic separation and quantification of the components. This method produces accurate results with high specificity for the compound of interest, but is time consuming and labour intensive. Also, because of the large number of steps in the process there is a significant chance of errors in sample preparation impacting the results. This method has good sensitivity and selectivity and accuracy for the target compounds but is limited in that the chemical balance the chemicals exist in inside the animal is disrupted during sampling. In many cases this disruption reduces the value of the results obtained, and in some cases makes this technique inappropriate for the analysis. Where the blood volume removed is a high proportion of the total blood volume of the animal, as is commonly the case when mice are used, the death of the animal results. This means that a different animal must be used for each data point and each repeat. By eliminating the need for a blood draw in this case, fewer animals would be required for testing and a significant improvement in inter-animal variation in the results would be achieved.

Alternatively biosensors have been developed for some applications in analysis of chemical concentrations inside animals. In this case a device consisting of a specific sensing element with associated transducer is implanted and produces a signal collected by an electronic data logger that is proportional to the chemicals to which the sensor responds. The main limitations of this type of device are that they normally respond to a spectrum of chemicals rather than having specificity for only one chemical. Of the spectrum of chemicals to which the sensor responds, some produce a greater and some a lesser response. Sensors are also susceptible to interferences where another chemical present in a system interferes with the response produced by the target chemicals. For these reasons biosensors are normally limited in terms of accuracy and precision. Finally biosensors are typically not as sensitive to low chemical concentrations as state of the art stand alone detectors such as mass spectrometers that are used in the above mentioned conventional analysis techniques and in solid phase microextraction. A strength of this technology is that the chemical balance in the system under study is not disturbed.

The in vivo procedure described here is a significant departure from conventional 'sampling' techniques, where a portion of the system under study is removed from its natural environment and the compounds of interest extracted and analyzed in a laboratory environment. There are two main motivations for exploring these types of configurations. The first is the desire to study chemical processes in association with the normal biochemical milieu of a living system, and the second is the lack of availability or impracticality frequently associated with size of removing suitable samples for study from the living system. Newer approaches that extend the applicability of conventional SPME technology, where an externally coated extraction phase on a micro fibre is used, seem to be logical targets for the development of such tools. As with any microextraction, because compounds of interest are not exhaustively removed from the investigated system, conditions can be devised where only a small proportion of the total compounds and none of the matrix are removed, thus avoiding a disturbance of the normal balance of chemical components. This could have a benefit in the non-destructive analysis of very small tissue sites or samples. Finally because extracted chemicals are separated chromatographically and quantified by highly sensitive analytical instruments, high accuracy, sensitivity and selectivity are achieved.

With the current commercially available SPME devices a stationary extraction polymer is coated onto a fused silica fibre. The coated portion of the fibre is typically 1 cm long and coatings have various thicknesses. The fibre is mounted into a stainless steel support tube and housed in a syringe-like device for ease of use. Extractions are performed by exposing the extraction polymer to a sample for a pre-determined time to allow sample components to come into equilibrium with the extraction phase. After extraction the fibre is removed to an analytical instrument (typically a gas or liquid chromatograph) where extracted components are desorbed and analysed. The amount of a component extracted is proportional to its concentration in the sample (J. Pawliszyn "Method and Device for Solid Phase Microextraction and Desorption", U.S. Pat. No. 5,691,206.).

To date commercial SPME devices have been used in some applications of direct analysis of living systems. For example they have been applied for the analysis of airborne pheromones and semiochemicals used in chemical communications by insects (Moneti, G.; Dani, F. R.; Pieraccini, G. T. S. *Rapid Commun. Mass Spectrom.* 1997, 11, 857-862.), (Frerot, B.; Malosse, C.; Cain, A. H. *J. High Resolut. Chromatogr.* 1997, 20, 340-342.) and frogs (Smith, B. P.; Zini, C. A.; Pawliszyn, J.; Tyler, M. J.; Hayasaka, Y.; Williams, B.; Caramao, E. B. *Chemistry and Ecology* 2000, 17, 215-225.) respectively. In these cases the living animals were non-invasively monitored over time by assessing the chemical concentrations in the air around the animal, providing a convenient means to study complicated dynamic processes without interference.

The current commercial devices do, however, have some limitations for in vivo analysis inside a living animal. Firstly, the application to chemical analysis inside animals requires greater robustness in both the extraction phase and the supporting fibre core. In addition, most of the extraction phases currently available are better suited for more volatile and less polar compounds. Only one phase is suitable for liquid chromatography (LC) applications (carbowax/templated resin). Analytes of interest that typically circulate in living systems are less volatile and more polar and require LC analysis, so new or modified extraction phases are indicated. The overall dimension of the current device is typically too large for direct in vivo analysis and for direct interfacing to microanalytical systems, the time required for the LC extraction phase to come into equilibrium with chemicals in a sample is relatively long (typically 1 hr or more in a well-stirred sample) and analysis is sensitive to degree of convection in the sample. Also the present SPME devices cannot be conveniently coupled to positioning devices necessary for in-vivo investigation at a well-defined part of the living system.

It is, therefore, desirable to provide a method and a device that allows minimally invasive sampling, quantification or analysis of a biological system.

SUMMARY OF THE INVENTION

It is an object of the present invention to obviate or mitigate at least one disadvantage of previous devices and methods for evaluating components of interest in biological systems.

The invention provides a method for measuring or identifying one or more component of interest in an animal or animal tissue, said method comprising the steps of: positioning a fibre within said animal or tissue, said fibre being at least partially coated with an extraction phase for adsorbing said one or more component of interest from said animal or tissue, said extraction phase being positioned within said animal or tissue; adsorbing said one or more component of interest onto the extraction phase for a pre-determined period of time; removing the fibre from said animal or tissue; and desorbing said one or more component of interest from the extraction phase into an analytical instrument for measurement or identification.

The invention further provides a device for adsorbing one or more component of interest from an animal or animal tissue, said device comprising: one or more fibre having an at least partially coated end, said end being at least partially coated with an extraction phase for absorbing one or more component of interest; and a positioning device for guiding the at least partially coated end of said fibre into position within the animal or animal tissue.

Additionally, the invention provides a method of measuring or identifying one or more component of interest in liquid samples arranged in a plurality of wells in a multiwell plate, said method comprising the following steps: simultaneously submerging a distal end of a plurality of fibres within said plurality of wells, respectively, the distal end of each fibre being at least partially coated with an extraction phase for adsorbing the component of interest from the liquid sample; adsorbing the component of interest onto the extraction phase for a predetermined period of time; removing the fibres simultaneously from the wells; and positioning the extraction phase into an analytical instrument for desorption, and measurement or identification of the component of interest.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
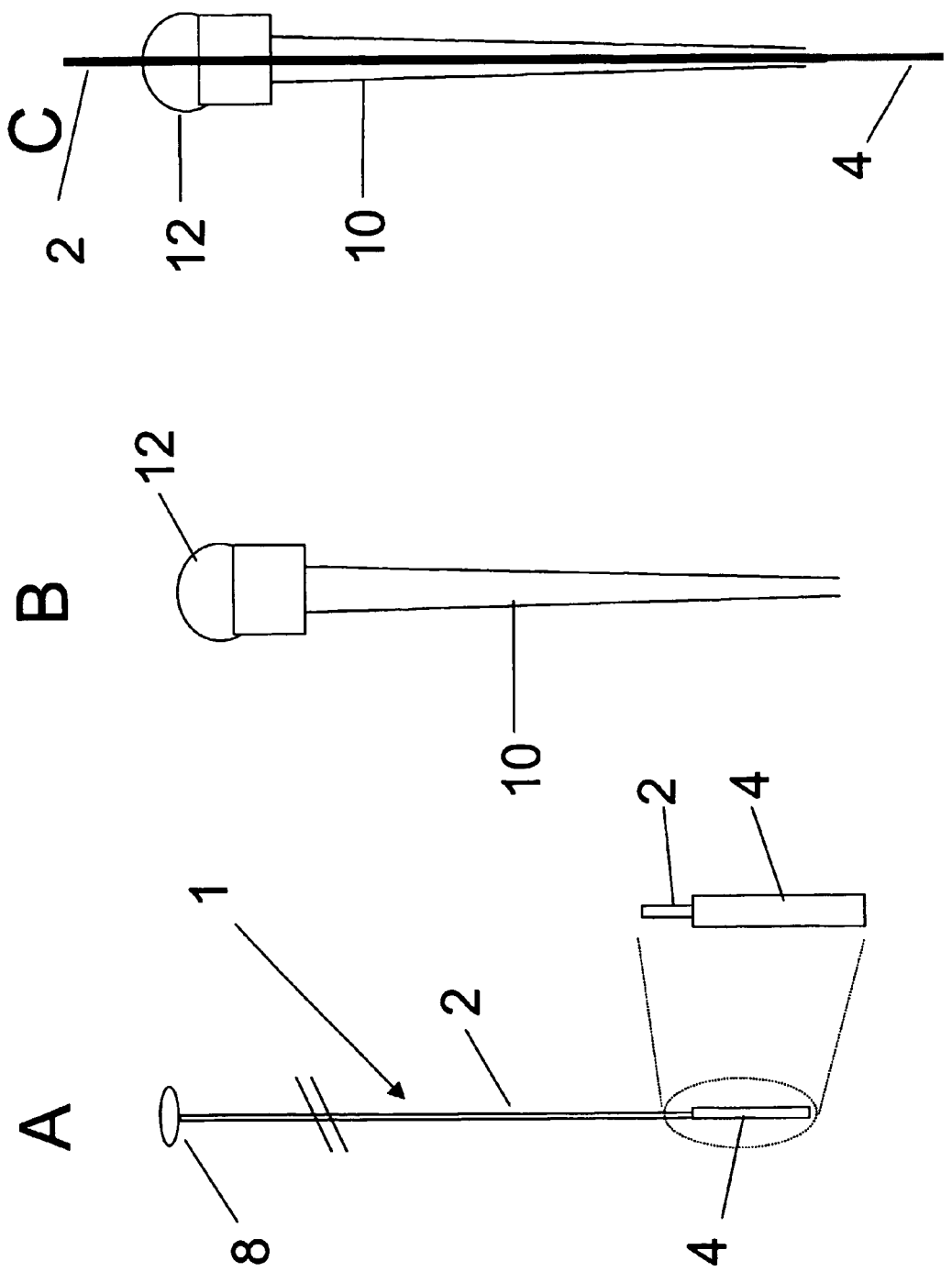
FIG. 1 shows a general schematic of device design according to an embodiment of the invention.

The invention relates to a method and micro-device based on coated fibre, optionally in combination with a positioning device, or separation and detection technologies particularly useful for in vivo studies of compounds of interest (identities and concentrations) in animals, or parts of animals.

The method for measuring or identifying one or more component of interest in an animal or animal tissue comprises the steps of: positioning a fibre within the animal or tissue, wherein the fibre is at least partially coated with an extraction phase for adsorbing the component of interest from the animal or tissue. The extraction phase is positioned within said animal or tissue, and thus the component of interest is adsorbed onto the extraction phase for a predetermined period of time. Following this, the fibre is removed from the animal or tissue; and the component of interest is desorbed from the extraction phase into an analytical instrument for measurement or identification. The method of the invention may be used in pharmacokinetic studies, wherein observation of analyte levels in a biological system over time is desirable to conduct with little or no blood or biological fluid removal from the system. In the case where blood samples would normally be drawn periodically for pharmacokinetic studies, the invention advantageously allows similar observations without removal of blood volume from the subject.

The extraction phase may specifically adsorb the one or more component of interest, and is preferably located at a terminal end (or "distal" end) of the fibre.

The period of time for which the fibre is positioned within the animal or animal tissue can be any acceptable time allowing adsorption of a detectable amount of the component of interest. For example, this time may be equivalent to equilibration time for a component of interest, or it can be less than equilibration time for a component of interest.

The component of interest can be any desirable component. For example, it may be a bacteria, viruses, sub-cellular components, biopolymers, DNA, proteins, drugs, drug metabolites, hormones, vitamins, environmental contaminants, chemicals, or cells. Any component capable of detection can be selected.

The animal or animal tissue can be is selected from the group consisting of single cell animals, live eggs, mice, rats, rabbits, dogs, sheep, pigs, monkeys and humans. As discussed further herein, an embodiment of the invention requires only samples, and is not necessarily conducted in an animal or in animal tissue. The animal tissue could be, for example, isolated cells and organs.

The fibre may be positioned within a blood vessel, and this embodiment would allow analysis of a component of interest adsorbed from blood flowing through said blood vessel. Optionally, the step of positioning said fibre comprises guiding the fibre into position within the blood vessel using a catheter. Other areas in an animal in which the fibre may be positioned include a) muscle, brain, soft tissue, or organ of said animal; and the component of interest is adsorbed from interstitial fluid or intracellular fluid; b) an inner part of spine, scull or bone; and the component of interest can be adsorbed from the bone, inner fluids including spinal fluid, bone marrow or brain fluid; or c) a cell of an animal, and an adsorbed component is extracted from the inner cellular fluid or sub-cellular component of a single cell of an animal. Of course, the invention is not limited to these examples.

During positioning, the fibre may be disposed within a housing having a sealed penetrating end. In this case, the method may include the step of opening the penetrating end once the fibre is positioned as desired within the animal, exposing the extraction phase within said animal.

Alternatively, the fibre may be inactive during said positioning followed by activating the extraction phase using change of electrical potential or optical means to allow adsorption of said component of interest. An example of this could be if the fibre is made of a metal which can be activated to attract certain components. Other possibilities for electrical activation of the fibre are within the scope of the invention.

The invention may use one fibre, or a plurality of fibres arranged as an array or bundle. As used herein, discussion of a fibre in the singular does not preclude the use of more than one fibre, or a bundle of fibres. In the case where a plurality of fibres are used, they may be disposed in a single position within the animal, or they may be disposed in more than one position within said animal, so as to obtain readings from multiple locations simultaneously. The fibre may be one or more optical fibres, such as a bundle of optical fibres.

In one embodiment of the invention, the extraction phase may additionally comprise a strongly bound calibrant which is retained in the extraction phase during the step of adsorbing. Alternatively, a weakly bound calibrant can be used which is released from the extraction phase during the step of adsorbing according to convection conditions and diffusion coefficient. The amount of the weakly bound calibrant remaining after the predetermined period of time can be observed. This can also be used to deliver a desired compound to the animal or animal tissue.

In another embodiment, a strongly bound reagent may be added to the extraction phase prior to extraction. This reagent may be a strongly bound reagent which reacts with the component of interest. An example of such a strongly bound reagent is one that labels the component of interest with a fluorescence tag. Another example is a reagent such as an enzyme, in which case the component of interest may be a substrate for that enzyme. Such an enzyme may be one that digests a protein directly onto the fibre, for example trypsin or a trypsin cofactor. Further, the reagent may be added to the extraction phase after the step of adsorbing, in which case the reagent subsequently reacts with the component of interest.

The reagent can be added to the extraction phase by spraying or dipping the reagent onto the extraction phase.

The method of the invention may be one in which a polymerase chain reaction (PCR) is conducted directly on the extraction phase. In such an embodiment, the components of interest are DNA or DNA fragments, the fibre is subject to periodic cycles of alternating cooling and heating, the reagent comprises polymerase and nucleic acids, and the method results in a polymerase chain reaction (PCR) on the extraction phase.

The reagent may comprise an ionization matrix utilized in matrix assisted laser desorption and ionization (MALDI). MALDI analysis of the extraction phase can be conducted with any embodiment of the invention amenable to such a method of measurement or compound identification. Any number of analytical instruments may be used with the invention, such as a spectrometer such as a time of flight instrument mass spectrometer (TOFMS) or an ion mobility spectrometer. After desorbing the component of interest from the extraction phase, measurement or identification of the component may occur in an analytical instrument such as a gas chromatograph, a liquid chromatograph, a capillary electrophoresis instrument, a capillary electrochromatography instrument and a microfluidic device.

The invention may include positioning of the fibre in an analytical instrument after the step of adsorbing. This could, for example involve laser irradiation of the fibre to desorb the component of interest from the extraction phase into the analytical instrument. In such a case, the fibre can be irradiated in a region not coated with the extraction phase, so as to desorb the component.

The invention may allow introduction of the fibre directly into a mass spectrometer prior to the step of desorbing. The fibre may be introduced into a mass spectrometer by insertion into a small solvent volume in a nanospray needle, followed by the step of desorbing, and electrospray of a desorbed component of interest.

After removing the fibre from the animal or tissue, the fibre may be exposed to a high voltage resulting in field desorption of the component of interest directly from the extraction phase into the mass spectrometer.

Separation of components of interest from the extraction phase may occur directly in a separation capillary or channel of the analytical instrument. The step of desorbing may be conducted in a small bore cartridge filled with a desorption solvent following by automated measurement or identification of a component of interest in the analytical instrument. In such a case, the fibre may be placed in the small bore cartridge immediately following the step of removing the fibre from the animal or tissue, and the cartridge can either be analysed immediately or sealed and transported or stored prior to automated measurement or identification.

The invention also relates to a device for adsorbing one or more component of interest from an animal or animal tissue. The device comprises one or more fibre having an at least partially coated end. The end is at least partially coated with an extraction phase for absorbing one or more component of interest. The device also includes a positioning device for guiding the at least partially coated end of the fibre into position within the animal or animal tissue.

Optionally, the fibre diameter can be of millimeter to nanometer dimensions, and formed of any acceptable material that would be amenable for use in the intended application. Such materials may include fused silica, plastic, carbon or metal wire. The fibre may be a plurality of optical fibres formed from fused silica.

Optionally, the fibre may be a hollow tubing having the extraction phase coated on an inside surface of the tubing. In this instance, the tubing may be in communication with a pump capable of draw up or ejecting a sample from the tubing. The pump may be of any acceptable type known for use with tubing. Alternatively, the fibre may be a hollow tubing having the extraction phase coated on an outside surface thereof. In this case, the tubing could be sealed at one end and have a pump in communication with the tubing to blow fluid, such as a gas or liquid, into the tubing. This would allow expansion of the tubing as desired, which could increase the surface area of the extraction phase as required.

The device of the invention may additionally comprise a sheath surrounding the fibre for protection and easy handling.

The extraction phase is advantageously biocompatible, as necessary. Optionally, the fibre may be additionally at least partially coated with a biocompatible protection layer, which can surround the extraction phase. Such a biocompatible protection layer may comprise polypyrrole or derivatised cellulose, or any such polymer as would provide protection.

The extraction phase itself may comprises any composition capable of binding a component of interest. It may, for example be a polymeric composition such as substituted or unsubstituted poly (dimethylsiloxane), polyacrylate, poly (ethylene glycol) or polypyrrole. Alternatively, the extraction phase may have a bioaffinity agent on its surface, such as a selective cavity, a molecular recognition moiety, a molecularly imprinted polymer, or an immobilized antibody. The extraction phase may contain any of these in combination.

The extraction phase can, alternatively be an extraction and ionization matrix for MALDI-TOFMS analysis, and may contain a calibrant molecule, as discussed above.

The fibre may be contained in a housing closed at one end, for opening and exposing the fibre when appropriately positioned within the animal or animal tissue. Such a housing may be a sealed leaf structure, or any other such openable sealant.

The positioning device itself may a catheter, for those applications where the fibre is guided into a blood vessel, such as a vein, or other tubular biological structures, as discussed in more detail below. Further, the position device may be an x-y-z micro positioning stage, for those applications wherein a tissue can be positioned on such a stage, and its movement finely controlled. The positioning device comprises an automated system, which may be rendered attachable to the animal or animal tissue. The positioning device may additionally be used to position said fibre within an analytical instrument for desorption of the component of interest from the extraction phase. The positioning device can optionally be used to place the fibre directly inside a separation capillary or channel, and could be used to couple the fibre to a laser beam facilitating desorption of a component of interest from the extraction phase. The positioning device may be used to facilitate desorption of a component of interest into an analytical instrument.

In the case where a plurality of fibres are used, these fibres may have the same or a different extraction phase coated thereon, so that more than one component of interest can be detected. More than one extraction phase can be combined on a fibre, so that a variety of components of interest can be detected.

The device may additionally comprise an agitator to cause movement of the coated end of a fibre, for example axial or horizontal movement of the fibre. In the case where the fibre comprises hollow tubing having the extraction phase coated on an inside surface of the tubing, the agitator may force the tubing to draw up a sample into the tubing. This can be effected by mechanical means or by creating a pressure differential forcing the tubing to draw up a sample into the tubing. The agitator may comprise an inflatable balloon.

The invention further relates to a method of measuring or identifying one or more component of interest in liquid samples arranged in a plurality of wells in a multiwell plate. This involves simultaneously submerging a distal end of a plurality of fibres within the plurality of wells, respectively, the distal end of each fibre being at least partially coated with an extraction phase for adsorbing the component of interest from the liquid sample. Following this, the component of interest is adsorbed onto the extraction phase for a pre-determined period of time. The fibres are then simultaneously removed from the wells, and are positioned in an analytical instrument for desorption, and measurement or identification of the component of interest from the extraction phase. Such an analytical instrument may be any of the ones noted above, such as a MALDI analytical instrument or a multichannel micromachined microfuidic device.

The inventive device for measuring or identifying one or more component of interest from liquid samples arranged in a plurality of wells in a multiwell plate, for use with the method described herein comprises a plurality of fibres, each having an at least partially coated distal end, said end being at least partially coated with an extraction phase for absorbing the component of interest. A positioning device is used for guiding the coated distal end of said fibres into a submerged position within the plurality of wells of the multiwell plate, for removing said fibres from said wells, and for positioning said fibres into an analytical instrument.

According to one embodiment, a small sterile device containing a small diameter fibre with an associated extraction phase coated thereon is used. The extraction phase has affinity for one or more compounds of interest. After exposure of the extraction phase in vivo, the device may be removed for quantitative or qualitative analysis in an analytical instrument.

A device for in vivo study of chemical concentrations consists of a fibre or wire and associated extraction phase. The fibre or wire may be made of fused silica, metal, carbon, graphite or a polymeric material. The device may or may not have an attached or removable handle. The device may have an associated or removable housing such as an outer needle sheath to provide access for the device to the tissue under study. Preferably the device is introduced to the tissue under study via a standard medical positioning device such as a catheter or microdialysis cannula. After extraction the housing may be retained if it is used in association with desorption, or discarded if it is not so-needed. Where a medical device is used to provide access to the tissue under study, multiple devices may be used with a single catheter for instance, obviating the need to puncture the skin or other tissues separately for each extraction.

A process of carrying out in vivo solid phase microextraction uses a fibre with associated extraction phase, which may or may not have an associated housing. In any case a means is provided to position the device in the tissue for the desired extraction. For extraction the device is left in contact with the tissue under study for a sufficient period of time to allow equilibration with the chemicals in the tissue, insensitivity to convective forces and/or maximal sensitivity. It is likely the device could be used to monitor chemical concentrations in humans or experimental animals such as rats, mice, dogs, sheep or rabbits. Subsequent to sampling the device is placed in an appropriate analytical instrument or desorption device so that at least one chemical component extracted is desorbed for quantification.

The device and process described are used to monitor chemical concentrations in vivo in a living animal, without causing a disruption in the dynamic balance in the animal systems. Some specific benefits can be described. Because no blood need be drawn for the analysis, animals are less stressed. This would allow for more data points to be collected for pharmacokinetic profiles, allowing for better data on which to make drug design decisions. It would also allow or for sampling of blood or tissue drug concentrations at multiple sites in an animal, to better assess the effects of differing metabolic processes in different locations in animals. Where more data points are collected from one animal, a reduction in inter-animal variation in the results arises. This variation can often obscure real pharmacokinetic trends and so by eliminating it, better pharmacokinetic data can be collected. Conventional sampling where a specific sample of blood/tissue is removed from an animal causes a disruption in the normal chemical balance of the animal. Each successive sample enhances the impact on the normal dynamics of the animal. With sampling according to the invention, where only a negligible portion of the analytes of interest are removed, the normal chemical balance remains unperturbed, thus eliminating the effect of sampling itself on the results. Genetic variation in drug metabolism within a population gives rise to differing pharmacokinetics for the same drug among individuals. The device and process described would be beneficial both in monitoring the effect of genetic variation on metabolism of existing drugs, and for directing the design of novel drugs to take advantage of variable genetic profiles for tailored drug design.

Calibration of the device may be achieved in several ways. Where equilibrium extraction is achieved, calibration by comparison to matched in vitro samples is simple and effective. Under non-equilibrium extraction or where it is not possible to match in vitro samples to the in vivo system, calibration may be achieved by pre-loading the fibre with a suitable calibrant. Direct quantification based on analyte physico chemical properties is also possible using spectroscopic analysis of the analytes directly from the fibre.

The device accomplishes both sampling and sample preparation during in vivo analyte extraction. Sample preparation may be limited to isolation from sample matrix and concentration in the extraction phase. It may also include additional processing on the fibre. Examples of this are derivatization of analyte to a form with higher sensitivity in detection through either a modification of product polarity or fluorescent tagging, amplification of analyte copy number in the case of DNA analysis to improve signal intensity, and protein or enzymatic digestion in the case of general biomolecules (eg. proteins) to convert them to a form more amenable to instrumental analysis (eg. peptide fragments). In all cases the goal of this on-fibre processing is to enhance detection/quantification of the target analytes.

In the conventional SPME device the overriding goal in device design was optimizing the affinity of the analyte for the extraction phase on the fibre, to maximize analytical sensitivity. In the case of in vivo analysis the issue of coating biocompatibility is equally important. Device design must take into account both biocompatibility and affinity in the extraction phase.

Because of the simplicity inherent in both the device design and the process, multiplexing in both sampling and analysis is much more practical that it has been for conventional analyses. Fibres may be grouped together in bundles, with fibres having either the same or different coatings, allowing for both sampling and quantification from many fibres at once, rather than one at a time.

Another advantage of the device and process is that quantification is performed separately from sampling, using conventional high sensitivity instrumental analysis. This allows better sensitivity and selectivity than are achievable where the detection is coupled directly to the sampling/sample preparation as is the case for biosensors. An interface is used to couple the fibre to the analytical instrument. This may be as simple as the off-line desorption of analytes into solvent filled wells in a multi-well plate, to a more sophisticated dedicated interface for thermal, field, solvent or laser desorption. In the case of a dedicated interface for solvent desorption, small internal diameter coupled with efficient solvent flow enhance desorption kinetics so that analytes may be removed from the fibre as quickly as possible.

Although the discussion thus far has focused on using a device without compounds of interest initially loaded into the extraction phase, to investigate chemical concentrations in a living system, the device described is equally suited to the delivery of a precise amount of a chemical compound to a precisely targeted tissue. If a device is first loaded with a pre-determined amount of compound of interest, it can be accurately positioned at the site of interest, where compounds will move out of the device according to kinetic and/or thermodynamic principles and thus supply the chemical to the tissue. This would be of value in targeted drug dosing where only a specific tissue is exposed to a drug compound.

FIG. 1, part A illustrates an extraction device 1 consists essentially of an extraction phase 4 coated on a fibre or wire 2 to be used with a positioning device to accurately locate the device in a tissue. The entire device is sterilizable by one or more of the conventional means of sterilization, such as autoclave, ethylene oxide, UV or gamma irradiation. The uncoated end of the wire may or may not include a handle 8 to facilitate positioning of the device. The length of the wire is variable depending on the application requirements. The extraction phase 4 could be a polymeric layer prepared on the wire surface, particulate adsorptive or absorptive material glued or otherwise affixed to the wire surface, or immobilized biorecognition agents such as antibodies nucleotides or protein receptors. When constructed of the stainless steel wire described below the extraction device is quite flexible. It will follow curves in a vein or catheter and normally resume a straight configuration when removed. The device is useful for the application of monitoring concentrations of drugs and their metabolites in blood or other tissues, either in single point monitoring or in multiple point (time course) monitoring.

FIG. 1, part B illustrates standard medical catheter is shown in schematic form having a catheter body 10 and a sealing septum 12 (PRN). PRN is the commonly used term for an i.v. adapter to seal a catheter, incorporating a piercable septum, marketed by Beckton Dickinson. In the text that follows applications are described that use such a catheter for intra venous (i.v.) sampling. In practice, catheters are available for accessing other vessels as well, so applications are not limited to i.v. ones. For instance arteries, vessels within organs or capillaries may also be accessed using similar devices.

FIG. 1, part C, illustrates an embodiment comprising the extraction device alone with no support rod and no handle may be introduced to a blood vessel through a previously placed medical catheter 10 with attached PRN 12. The end of the extraction device with the extraction phase 4 may be contained in a sterile hypodermic needle that is used to pierce the PRN and provide access to the catheter. The extraction device is pushed partly into the catheter by means of the support wire 2 and the hypodermic needle is withdrawn. In this case the PRN provides a seal around the device to prevent blood loss. The extraction device 1 is then pushed into the catheter and blood vessel by an appropriate amount so that the extraction phase is exposed to the flowing blood. The catheter is then flushed with saline to prevent clotting in the catheter. After the required time for the extraction of drugs and metabolites the hypodermic needle is once again used to pierce the PRN to provide a port for removal of the extraction device. The extraction device is then removed from the housing, rinsed and packaged for transport for analysis. The coated fibre can be placed inside a micro-syringe as described in U.S. Pat. No. 5,691,206, for easier handling with a catheter or other positioning device.

Figure 2:
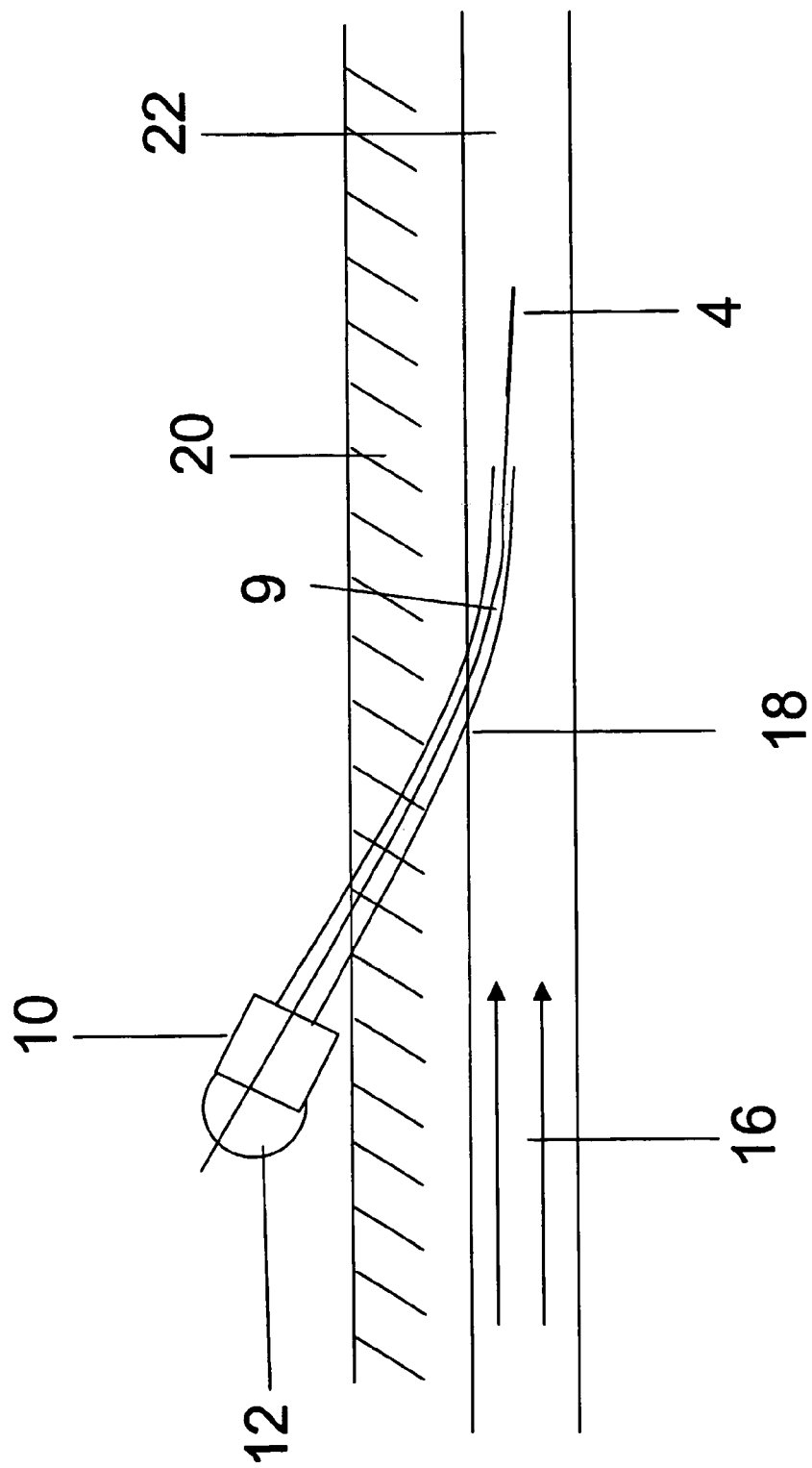
FIG. 2 illustrates the use of a medical catheter to position device accurately within a vein.

FIG. 2 shows the use of a medical catheter 10 passing through the skin 20 and vein wall 18 to position the extraction device 9 with PRN 12 inside a vein 22 with blood flow 16 past the exposed extraction phase 4. In this position the extraction device has been fully depressed through catheter so that the extraction phase is fully exposed to flowing blood outside of catheter. PRN 12 is still accessible to allow for flushing to ensure patency of the catheter.

Figure 3:
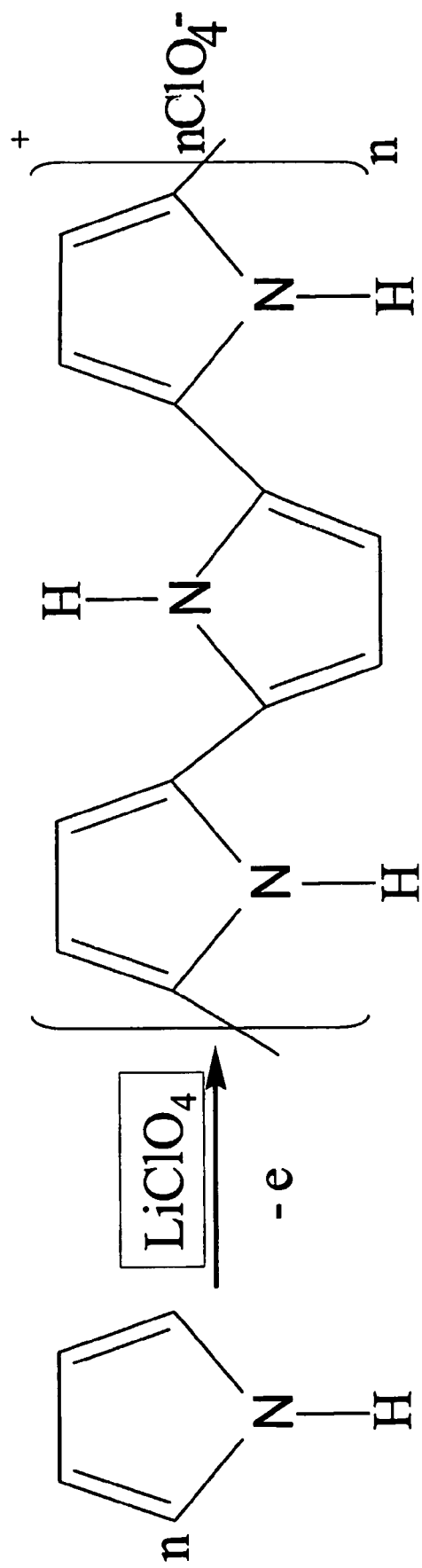
FIG. 3 shows a schematic of the polypyrrole polymerization reaction.

FIG. 3 illustrates a schematic of the polypyrrole polymerization reaction. As an example of an extraction phase, polypyrrole may be deposited onto the surface of a fine metal wire by electrolytic oxidation under conditions of controlled potential The polymer can be prepared on thin stainless steel wire as described below. The resulting polymer can then serve as the extraction phase to extract pre-concentrate drug compounds directly from blood flowing in a vessel. An exemplary preparation of coating a stainless steel wire with polypyrrole is provided in Example 1.

Medical Sampling Device

In use it may be desirable to provide a housing or sheath to allow access to the tissue site of interest. The housing is also important to ensure correct positioning of the device at a specific location in the tissue or site under study. This may be by puncture of the skin and/or blood vessel followed by positioning of the phase at a specific site for analysis, incorporation of multiple fibres and agitation means. The housing may also be required to provide a seal to prevent blood from escaping past the device during sampling. The nature of the associated housing will be dependent on the site to be sampled.

FIGS. 4 to 9 provide schematic illustration of options for the devices and described herein.

Figure 4:
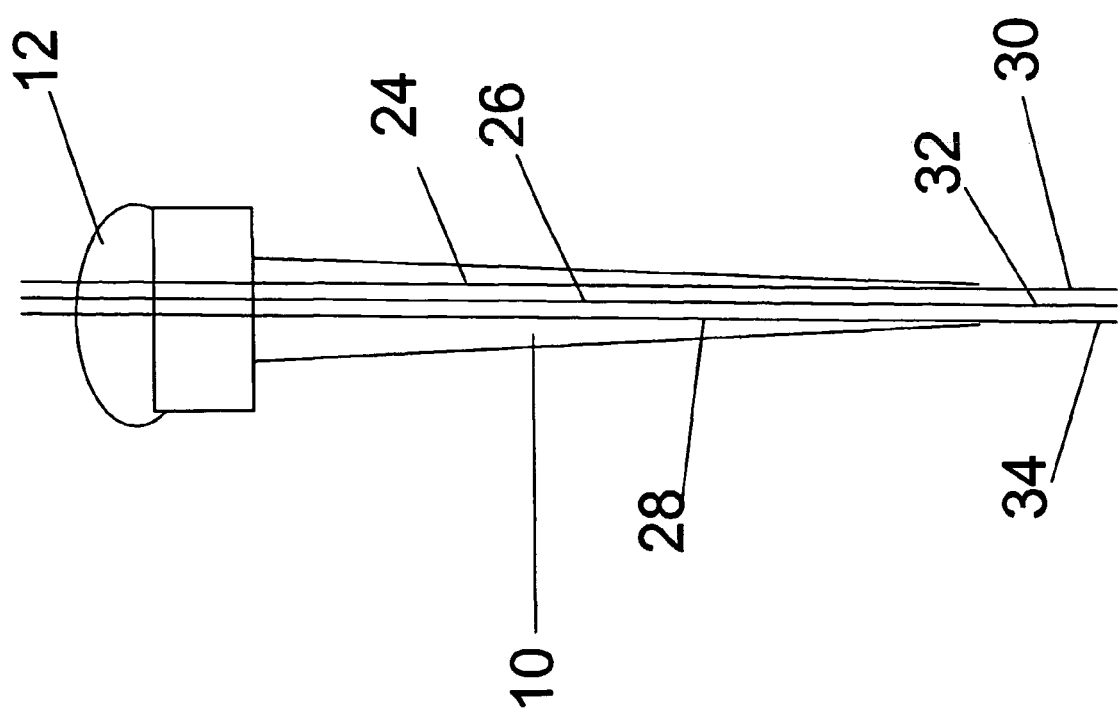
FIG. 4 is a schematic of a catheter with multiple coated fibres.

FIG. 4 shows modifications to the device and a housing for multi-fibre sampling using a commercial catheter. Fibres 24, 26 and 28 are coated by coating 30, 32 and 34 respectively, which can be the same type of coating to increase capacity of the device, or preferentially each fibre having different highly selective coatings, such as antibodies designed to recognized only defined components of interests in a living animal.

The device may also be used for sampling from an unpressurized medical port such as a microdialysis cannula. Because such a port is not pressurized, there is no need for a seal to prevent fluid from flushing past the device during sampling, which obviates the need for an additional sheath or specialized housing during sampling. The device has significant advantages over conventional microdialysis sampling because it is not necessary to either add or remove fluid from the tissue to sample. In conventional microdialysis analysis a portion of the fluid that diffuses into the cannula from the surrounding tissue may be removed for analysis. Alternatively synthetic fluid is pumped into the cannula and then to an analytical instrument for semi-continuous monitoring. In both instances the fluid balance of the tissue is disrupted during sampling, by reduction in volume in the first instance and by dilution in the second. Analysis using the device according to the invention would not disrupt the biochemical balance in the tissue as it does not cause such an imbalance.

Figure 5:
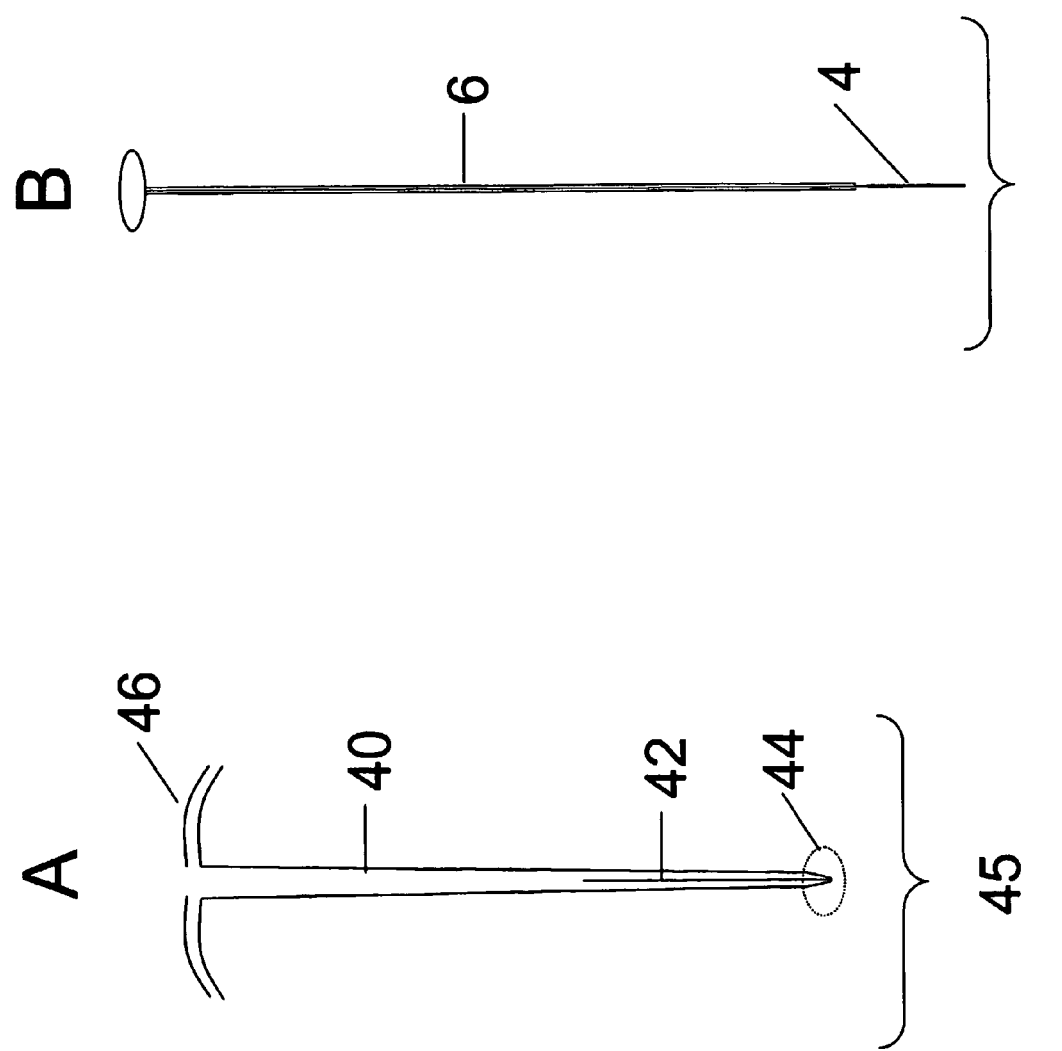
FIG. 5 shows a schematic of housing and device for soft tissue sampling.

FIG. 5 shows a modified housing in part A and extraction device in part B appropriate for sampling directly from soft tissue. When the device is in the retracted position the housing as seen in FIG. 5, part A, is constructed of a rigid tube 40 with a handle 46 and has a sealed tip 44 for penetrating soft tissue. The tip is constructed from two or more leaves separated from each other part way up the housing by a cut or slot 42 and are normally held together by spring action to seal the tip. FIG. 5, part B shows the extraction device supported in a thick tubing 6 for opening up the leaves of the needle end to allow exposure of extraction phase for sampling.

Figure 6:
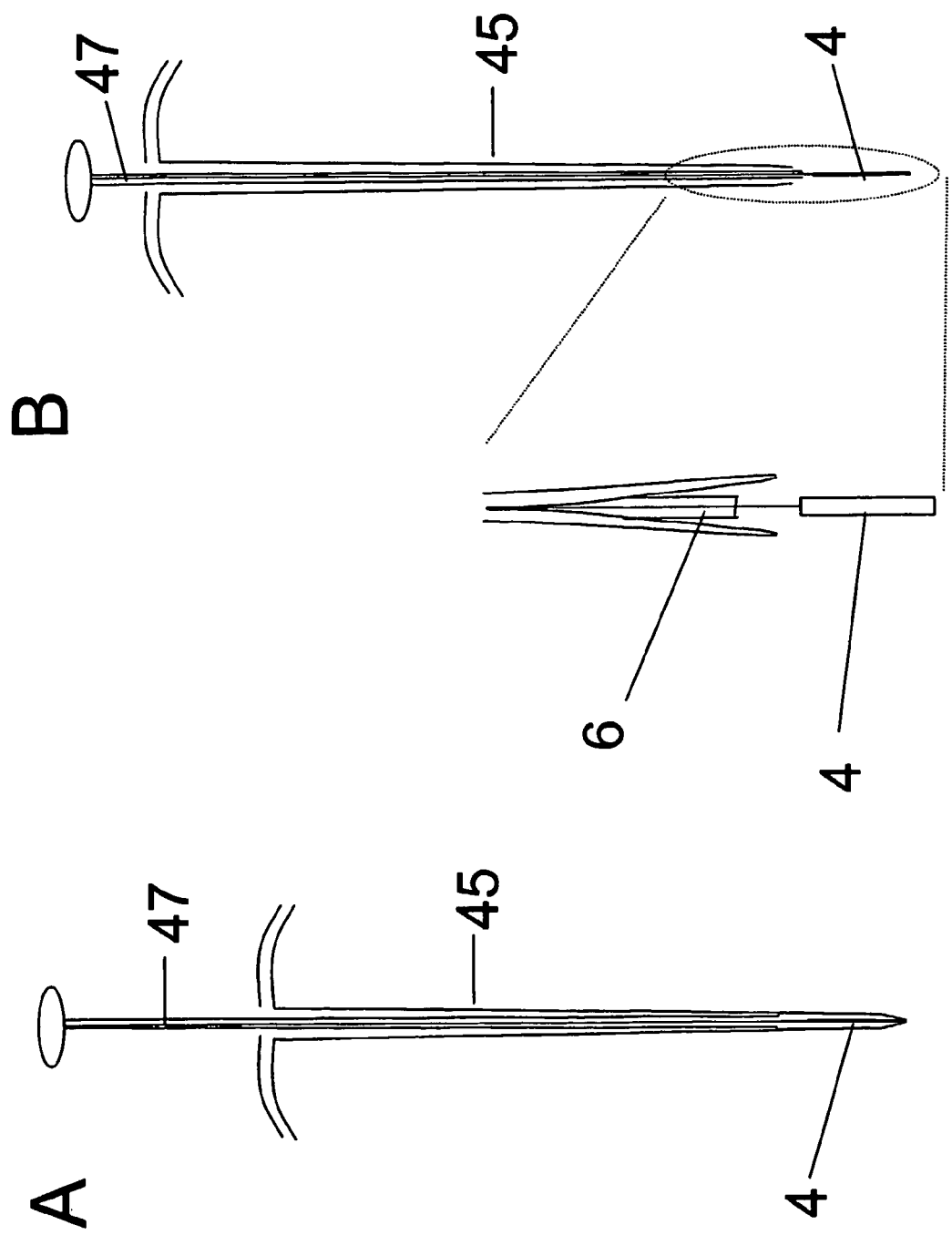
FIG. 6 illustrates operation of housing and device for soft tissue sampling.

FIG. 6 shows a schematic of the use of the extraction device and housing for soft tissue sampling. FIG. 6, part A, shows the extraction device 47 within the housing 45 in retracted position. FIG. 6, part B, shows the extraction device 47 in the housing 45 in exposed position. The supporting wire 6 moves with extraction device to force open the leaves at tip of needle to allow extraction phase on wire to pass through.

Figure 7:
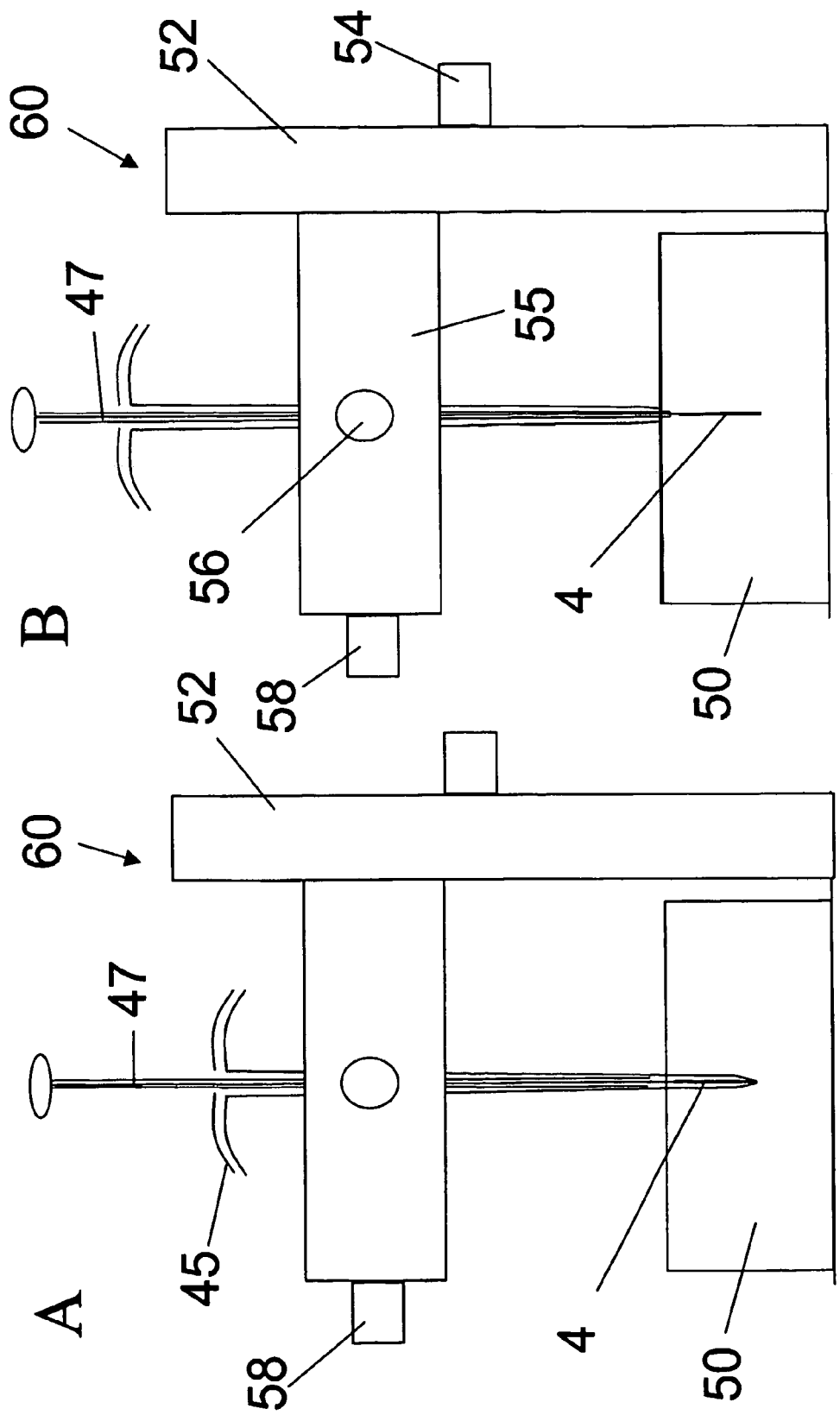
FIG. 7 shows a schematic of use of soft tissue sampling housing to position device for sampling with x-y-z stage.

FIG. 7 illustrates the housing 45 and extraction device mounted in the x-y-z positioning device 60 consisting of the "z" vertical positioning stage 52 with high resolution dial 54 and the x-y stage 55 with appropriate dials 56 and 58 allowing precise positioning of the extraction phase 4 within the sample 50. This positioning system is typically with microscope to monitor insertion and sampling process. The housing is first used to prepare a channel for the device at the required position for sampling (FIG. 7, part A). The housing is then withdrawn slightly while the extraction device 47 is held still. In this way the extraction phase of the device comes into contact with the tissue surrounding the channel prepared by the housing, thus avoiding a plug of tissue from traveling into the housing, and avoiding having the extraction device itself have to bore the channel in the tissue. In this case the device is used to monitor the concentrations of chemicals in the interstital or intracellular fluids in the tissues, as it would not sample chemical that is bound to tissue proteins or membranes. This would be preferred to tissue biopsy both in terms of the simplified sampling and reduced tissue damage.

Figure 8:
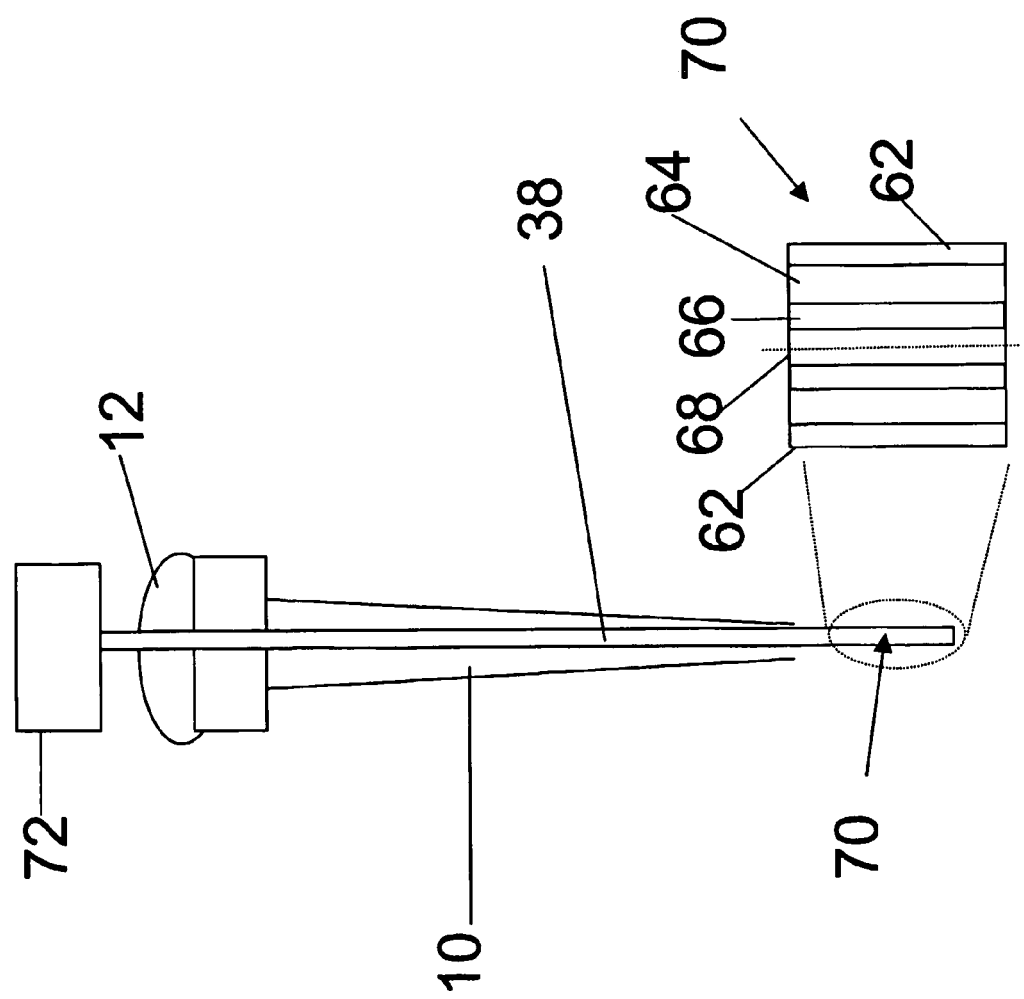
FIG. 8 illustrates a device according to an embodiment of the invention with hollow fibre with inner coated surface with catheter positioning device.

FIG. 8 shows the catheter with the hollow fibre 38 coated on the inside wall surface at the lower portion 70 of the fibre. The schematic cross sectional view shows the two layer coating 66 and 64 on the inner fibre surface 62. The outer coating 66 is chosen to be biocompatible to eliminate absorption of proteins, while the inner coating 64 is the extraction phase facilitating removal of well defined components from sample introduced to the inner fibre via channel 68. The sample is drawn into the hollow fibre by using the device 72 generating pressure differential, such as syringe or metering pump connected to the hollow fibre. The action of drawing and ejecting sample produces agitation and therefore accelerate the extraction rate. The tubing is mounted in catheter, but can also be mounted in a positioning device illustrated in FIG. 7.

Figure 9:
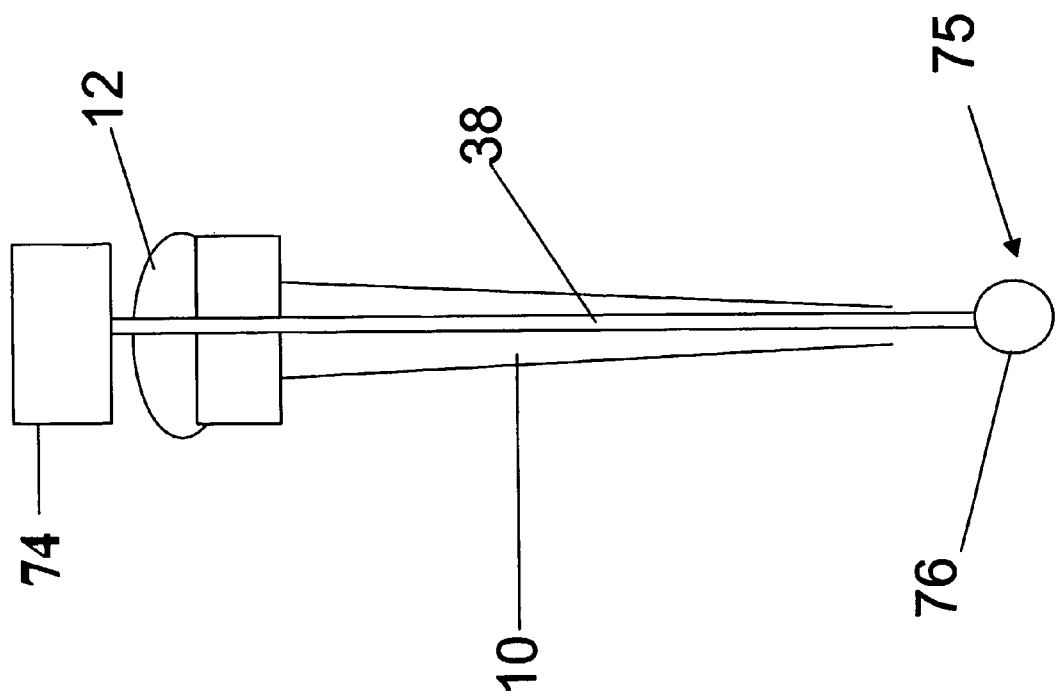
FIG. 9 illustrates a device according to an embodiment of the invention with hollow fibre sealed at one end with flexible extraction phase.

FIG. 9 shows the catheter with the hollow fibre 38 and stretchable coating sealing one end that can be blown out forming a small balloon structure 75 using the pressurized gas delivery device 74, such as small compressor or cylinder with carbon dioxide and micro-regulator connected to the free end of the hollow fibre. The material of the coating or its modified surface 76 can be designed to extract compounds from sample. The expended coating has higher surface area resulting in extraction rate enhancement. In addition repeated expansion and retraction of the coating cause induction of the convection currents and further increase in the extraction rate.

Miniaturization

While the device described is quite small (127 μm diameter), further miniaturization would be beneficial, particularly for the study of single cells. As probe size is reduced, the effect of the size of the theoretical boundary layer around the extraction phase on the rate of extraction is diminished, as is the case with microelectrodes (Heinze, J. *Angew. Chem. Int. Ed. Engl.* 1993, 32, 1268-1288.). In practical terms, this means the degree of convection in the sample has less effect on the rate of extraction. This is important for sampling of any system where static extraction must be conducted, as it would in single cells, or where degree of agitation is variable as it is for intravenous sampling. In addition, the dimension of the extraction phase also impacts extraction equilibration. Thinner extraction phases equilibrate faster and are less dependent on sample convection. Devices with overall dimensions in the range of 1-10 μm would be suitable for monitoring the interior of single cells while devices in the sub-micron range would be useful for monitoring organelles within cells. There are currently no feasible means to accurately assess chemical concentrations occurring within cells. All currently available methods either require that the cell is killed (eg. cell lysis followed by CE of cytosolic components in microchannels), which may produce an erroneous result, or suffer from poor accuracy (fluorescence tagging of specific compounds). The main strength of the coated fibre technology is that it can monitor cellular process in a non-disruptive manner. Only a negligible portion of the chemical is removed, allowing cellular processes to continue unperturbed. Commercially available micropositioning devices using x-y-z stage coupled to microscope can be used to position coated end of the fibre in the well defined part of the investigated system.

Technology that has been developed for genetic manipulation of cells uses fine capillaries to sample and introduce genetic material in cells, controlled by micromanipulators and monitored by stereomicroscopes. Cells are maintained in isotonic environments during the manipulations, typically by being contained in dishes or vials filled with suitable buffers. Similar instruments could be employed for positioning and sampling cells with fibre probes.

Portable Automated Sampling

Because the device and process described simplifies sampling and sample preparation significantly, it provides the opportunity for automated sampling of tissue concentrations without the need for continual human involvement. In on-line microdialysis sampling an animal being monitored is tethered to a stationary support and tubing conducting fluid to and from the microdialysis cannula and analytical instrument (CE or LC) is included in the tether. In the embodiment, an animal being monitored does not need to be tethered, but rather can carry a device for automatically moving probes in and out of a catheter, cannula or other sampling port at prescribed times. After sampling the device would hold the probes for retrieval and quantification at a later time. This embodiment would have similar advantages to the microdialysis system in terms of reduced human intervention and hence reduced sampling errors, with the additional advantage that animals in a study would be less restricted and stressed, and experiencing a more normal environment. This would reduce stress impacts on the integrity of the results.

Strategy of Single Use Devices

Up to now SPME devices have been designed to be re-used numerous times. While it is possible to re-use the polypyrrole coated fibre (wire) device described above, it is advantageous that this device be employed as a single-use device. Particularly in implementations where the device is exposed to blood, it would not be practical to clean the device and associated housing sufficiently for re-use. The goal of manufacture should be to minimize cost so that users find it cost-effective to dispose of the device after use.

Coating Strategies

There are a number of additional coating strategies that would be desirable in the design of these devices, under certain circumstances. These would extend the usefulness of the devices for the purposes described and allow them to be applied for additional purposes.

Improved biocompatibility in the extraction phase would be beneficial to extend either the time period the phase can be in contact with tissues, or increase the number of samplings that can be made from one site. This can be achieved in two different ways. Either new phase with better biocompatibility could be selected or a biocompatible outer layer could be used in conjunction with an inner extraction phase having lower biocompatibility.

Polypyrrole itself has good biocompatibility. It has been used for several years in biosensor devices without any evidence of toxicity, immunogenesis (initiation of an immune response) or thrombogenesis (initiation of clotting response). It is an example of an extraction phase that is suitable for exposing directly to the investigated system. If it is desirable to use a less biocompatible extraction phase the device could be rendered biocompatible by coating the extraction phase with an outer biocompatible layer such as derivatized cellulose. Analytes of interest would diffuse freely through this outer layer and be extracted by the extraction phase on the inner layer. This may be useful if more traditional extraction phases such as poly (dimethylsiloxane), polyacrylate or poly (ethylene glycol) are of interest for extractions.

Biorecognition entities that either comprise the extraction phase or are immobilized in another phase having low extraction affinity could provide both higher selectivity and higher sensitivity in these analyses. Higher affinity would provide higher sensitivity and more easily allow for shorter probe residence times. Higher selectivity would allow for reduced disturbance of the system under study, further enhancement of sensitivity and reduced concern for competition in extraction. This would permit the quantitative analysis of one compound present at low concentration when a competing compound is present at high concentration.

Biorecognition in the extraction phase may be accomplished by entrapment of antibodies or another molecules capable of biorecognition in an inert biocompatible extraction phase. This is demonstrated by the use of polypyrrole to entrap antibodies specific for diazepam.

Figure 10:
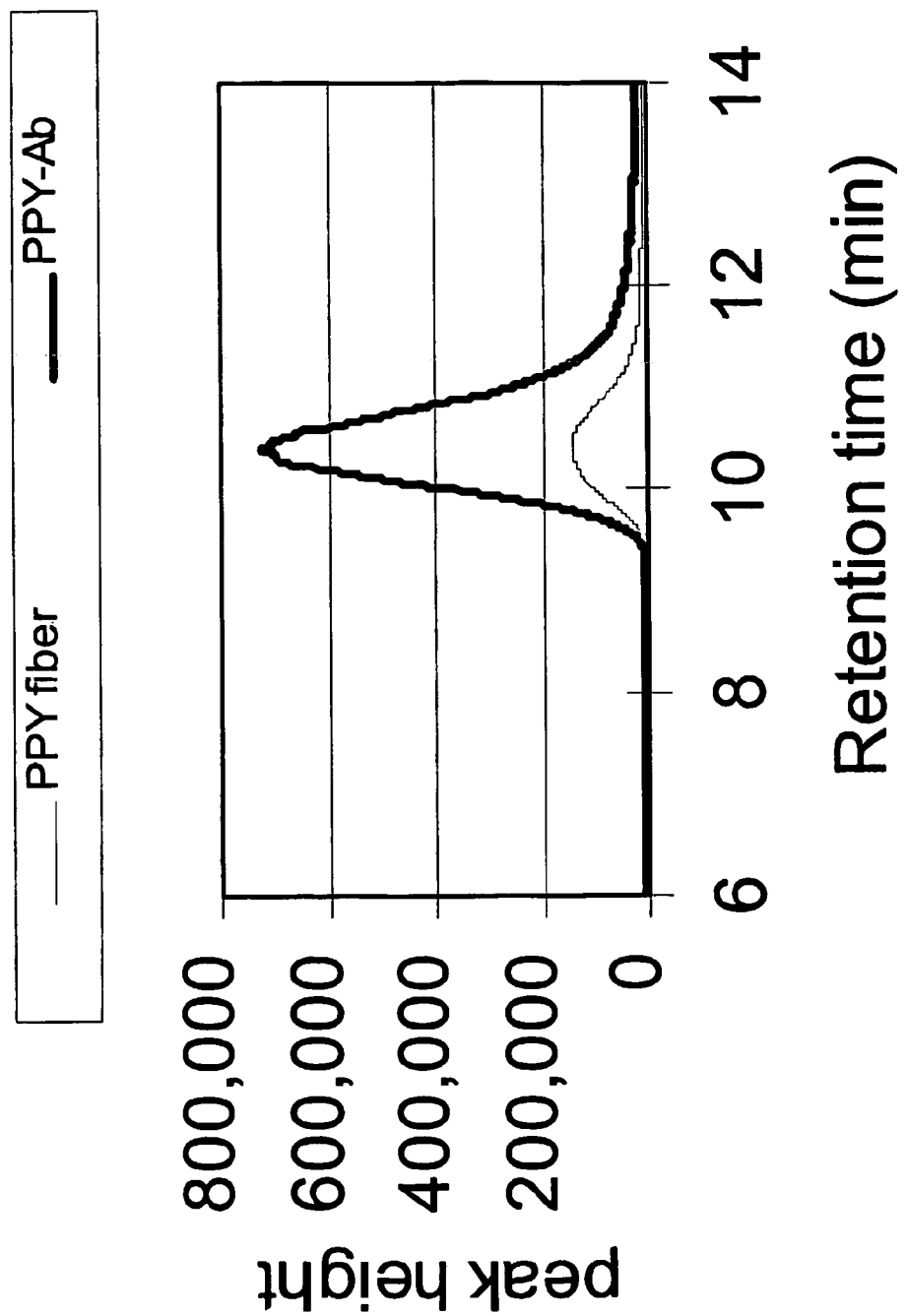
FIG. 10 shows a chromatogram comparing diazepam extraction from fibre with polypyrrole only versus fibre with anti-diazepam antibody entrapped in polypyrrole.

FIG. 10 shows a chromatogram comparing extraction of a sample containing diazepam, with a device with polypyrrole only, versus a device with entrapped anti-diazepam antibody. In this case the analyte affinity to the antibody is much higher than it is to the polypyrrole. Alternatively antibodies, nucleic acids or other molecules may be covalently attached to the fibre using typical immobilization strategies or they may be electrostatically immobilized by means similar to the immobilization of nucleic acid to nitrocellulose used in current blotting technologies. For covalent immobilization either random or oriented strategies may be used in one application or another.

Figure 11:
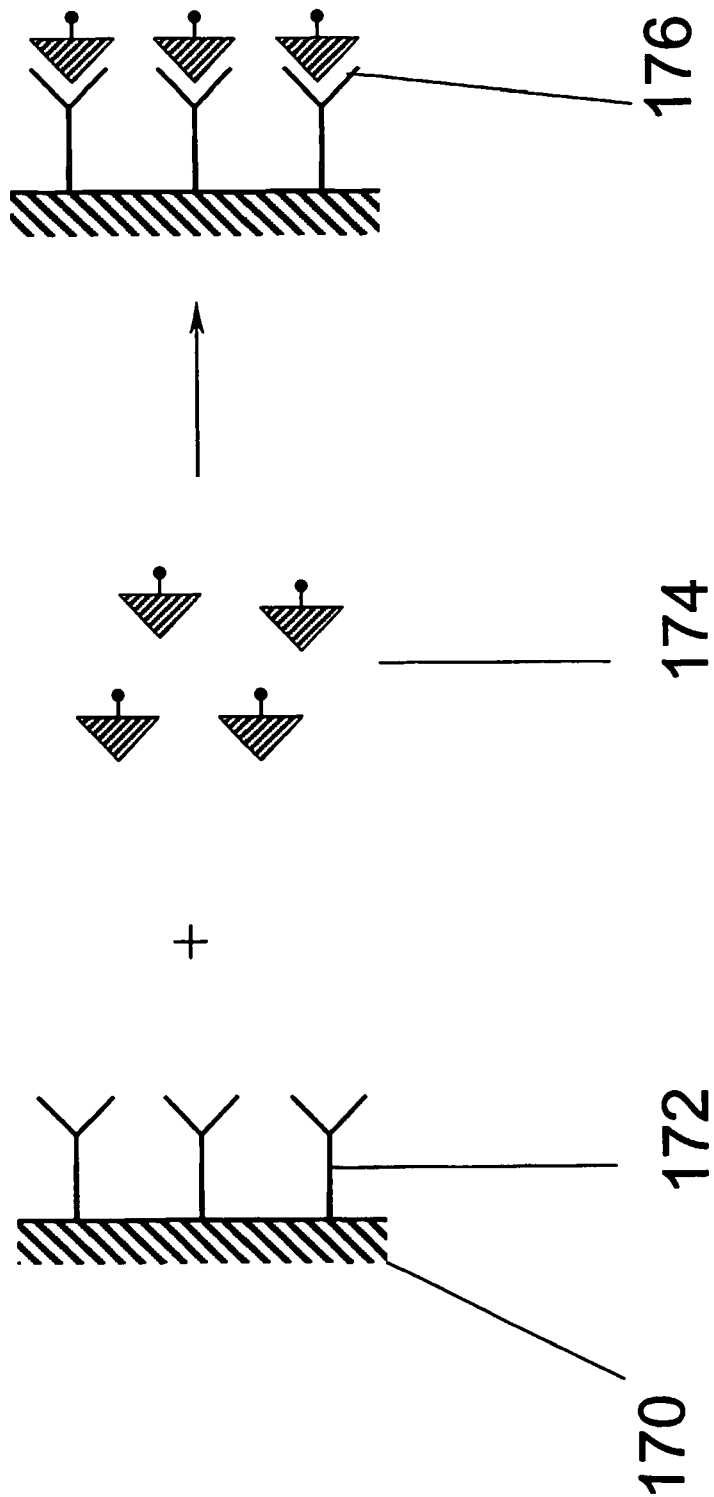
FIG. 11 illustrates selective extraction of diazepam using anti-diazepam antibodies immobilized on surface.

FIG. 11 shows a schematic of the oriented immobilization of antibody 172 on a surface 170, and attraction of antigen 174, to form an antibody-antigen complex 176. The diazepam may be liberated from the complex for quantification by temporary or permanent denaturation of the antibody protein.

If a probe with very high selectivity was developed, it could potentially extract only the compound of interest, which would eliminate the need for chromatography in the analysis. Direct introduction to a mass spectrometer for quantification would further simplify the analytical process. Such entities may include antibodies or antibody fragments, proteins, protein subunits or peptide sequences, DNA, RNA or polynucleotides or the antigens or substrates that bind with any of these. Such biorecognition entities may be immobilized by adsorption, electrostatically, covalently or by entrapment within another matrix. Covalent immobilization may be by either random or oriented means.

Biorecognition may also be achieved by using molecular imprinted polymers. In this case a polymer is prepared in the presence of the analyte of interest. The polymer contains functional groups that interact electrostatically with the analyte. After polymerization the analyte is removed and cavities remain in the polymer, with appropriate functional groups located inside. When used for extraction, analyte freely soluble in the sample is attracted to the cavities and held there by electrostatic forces. These polymers are seen by some as synthetic antibodies due to their high selectivity for the analyte of interest. Such polymers provide enhance selectivity when used as extraction phases in devices according to the invention.

It is also possible to prepare a coating that can have its extraction efficiency gated or activated just prior to extraction. This would allow for the pre-positioning of the device in a specific site, and then activate the extraction phase just as extraction is to start. Because polypyrrole is a conducting polymer, this may be accomplished by applying a small charge to the fibre. This is useful for the extraction of ionic compounds through controlling of the oxidation state of the polymer. Alternatively this may be accomplished using the device shown in FIG. 8 for soft tissue sampling. The device could first be positioned in the desired location, but the exposure of the fibre to the tissue could be delayed until the proper time to initiate sampling.

Use of Indicator Compound

A common and valuable tool in bioanalytical analysis is the monitoring of the appearance or disappearance of an indicator compound that is specific for a biochemical pathway. This is used for instance to monitor for the presence of specific cells or bacteria, or for the presence of free enzymes. In the typical chemical reaction a substrate (S) is transformed into a product (P) by interacting with a single enzyme or an enzyme system with associated cofactors. Enzymes may or may not be transformed in this process. The indicator may be the substrate, in which case its disappearance is monitored, or it may be the product, in which case its appearance is monitored. The amount of indicator formed in a specific time is correlated to both the amount and activity of the target enzyme present. If the indicator has an affinity for the extraction phase, enzyme activities and/or metabolic rates may be monitored in situ. The substrate may be either loaded onto the fibre or placed into a cell suspension or enzyme solution. When the fibre is placed into the solution, indicator will become immobilized in the fibre, and can be subsequently quantified by an analytical instrument.

Pre-Loading of Fibre with Calibrant

For conventional SPME analysis, a common difficulty is in devising accurate means of quantification. For in vitro analysis quantification is often achieved by adding a known amount of standard to the sample, and then performing the analysis. This is referred to as calibration by internal standard or standard addition. The amount of the standard recovered is assumed to be correlated with the amount of unknown analyte recovered and the ratio is calculated in order to determine the original concentration of unknown.

For in vivo and in situ analysis it is typically not practical to add a standard to the system under analysis. Until now the most practical means of calibration is by preparing a series of synthetic standards that match the sample as closely as possible, and comparing the results from the standards analysis with that of the unknown. This approach was described above for the calibration of polypyrrole devices in the in vivo pharmacokinetic study with reference to FIG. 12. In this case whole dog blood was obtained from a commercial supplier and samples were prepared with various drug concentrations. Upon analysis a calibration curve is constructed and this curve is used to interpolate unknown detector responses to estimate unknown drug concentrations. While the method is conceptually simple, it is not always highly accurate as it cannot accommodate the impact of slight changes in the in vivo site for impact on the results.

As an alternative to conventional internal standard calibration, a standard may be loaded onto the fibre (extraction phase) prior to analysis and the loss of standard from the fibre is monitored instrumentally. Where the kinetics of absorption of the internal standard analyte to the fibre is equivalent to the kinetics of desorption (binding is reversible), absorption and desorption are controlled by diffusion in the sample and the rate of loss of standard from the fibre will be correlated with uptake of analyte by the fibre. The amount of analyte lost may be correlated with the amount absorbed, and consequently with sample concentration of unknown also. Using this strategy variation in sample convection may be controlled for by referencing unknown analyte to the amount of calibrant lost from the fibre. Alternatively, where the convection conditions and hence rate of mass transfer are and are known or controlled, the use of an irreversibly bound calibrant on the fibre may be used. The fibre would first be exposed to a matrix-matched standard with a known concentration of analyte. The fibre would subsequently be exposed to the unknown sample. The ratio of unknown to standard extracted by the fibre would accurately reflect the ratio of unknown to standard sample concentrations. (G. Xiong, Y. Chen and J. Pawliszyn "On-site calibration method based on stepwise solid-phase microextraction", *J. Chromatogr.* in press).

Pre-loading of compound onto the fibre may also be used for calibrated delivery of compound to a precise tissue region. Where the compound pre-loaded has low to moderate affinity for the fibre, compound will partition out of the fibre and into the surrounding tissue during exposure. This may be used as a means of dosing only one targeted tissue region with a drug or other compound of interest, avoiding dosing of the whole animal as is commonly the case in therapeutic drug regimens. Tissue dosage control may be attained by precisely controlling the exposure time. Dosage may then be confirmed by desorbing remaining analytes into an analytical instrument to quantify the amount remaining, allowing the calculation of the amount delivered.

An exemplary use of calibrant is discussed below with reference to Example 4.

Use of Multiple Fibres

The development of multiple fibre coating strategies has several benefits. In addition to providing more flexibility in selecting devices for a particular application, multiple devices could be used in parallel to provide for a more complete profiling of the types and amounts of compounds present in a sample. This may be accomplished either by exposing multiple fibres to a sample in parallel, or by preparing one fibre with multiple sorbents.

Fibres for Conducting Micro-Chemical Reactions

On-fibre reaction can significantly enhance the detection of components of interests. For example on-fibre fluorescence labeling has been has improved detection limits for detection of toxins at trace level (A. Namera, A. So, J. Pawliszyn "Analysis of Anatoxin-a in Aqueous Samples by Solid-Phase Microextraction Coupled to High-Performance Liquid Chromatography with Fluorescence Detection and On-Fiber" Derivatization *J. Chromatogr.* 963, 295-302 (2002)). Two of the most important chemical reactions for molecular characterization in genomics and proteomics research are DNA amplification and enzymatic protein digestion. Both processes are enzymatic reactions that are conducted in vitro, with the products either being carried on to a further processing step or analysed directly.

In DNA amplification a small number of DNA or polynucleotide fragments are amplified by the enzyme DNA polymerase. Through the action of the enzyme and suitable substrates, the copy number of DNA fragments can be increased exponentially in just a few hours. The process is characterized by high fidelity so that the end product is a very pure solution of identical DNA fragments. Typically the amount of DNA originally present is insufficient for further processing and/or analytical characterization whereas the concentration in the final product is sufficient. The product may either be characterized for nucleotide content and sequence or used for the preparation of peptides or proteins coded by the DNA sequence.

For enzymatic protein digestion a protein sample is digested by enzymes that cleave the polypeptide chains at specific sites. The resulting polypeptide fragments may be characterized for molecular weight or peptide content and sequence. Typically the intact protein is too large for direct characterization and so a protein is characterized by a 'fingerprint' analysis of the pattern of polypeptide fragments produced by one or more enzymatic cleavages. Alternatively the polypeptides may be sequenced and the sequence of the original protein reconstructed. This allows for example, that the DNA sequence coding for the protein may be determined either for the purpose of identifying its location in the genome or for development of an expression system to produce the protein in quantity.

With the continued miniaturization of genomic and proteomic analyses through the use of micromachined or μTAS devices, there is a need to miniaturize the sample preparation and introduction steps that come up front. These types of miniaturized analyses are increasingly important in the fields of genomics and proteomics where sample sizes are small due to the high cost of these samples. Also the miniaturization allows for parallelization and higher throughput in analysis to more efficiently process the very large number of samples made possible by the completion of the human genome project. A porous polymer attached to a fine fibre or wire makes an ideal medium in which to conduct these enzymatic reactions in miniature scale, with the added advantage that when the reaction is complete, the device is also suitable for introduction of the reaction products directly to a microanalytical system.

Interfaces

As described above one of the strengths of the device and process described is that once sampling and sample preparation (pre-concentration and elimination of matrix) have been completed, the device of the instant invention is ideally suited for directly introducing the extracted analytes to an instrument for separation and quantification.

Conventional SPME devices are interfacing to GC or LC equipment for quantification of amount of compound extracted. In the case of GC equipment the fibre is exposed in the heated injection sleeve similarly to the way a conventional syringe injection is conducted. Analytes for GC analysis are necessarily volatile at the temperatures normally used in a GC injector and are efficiently desorbed in the hot carrier gas flowing through the injection sleeve and into the separation column. Compounds analysed by LC are typically non volatile and/or thermally unstable and so heat cannot be used for desorption. For LC desorption a dedicated interface is required to first remove analytes from the fibre and transfer them to a solvent. A portion or all of this solvent is then injected into the instrument for analysis. In the commercial interface the fibre is desorbed in a solvent filled chamber in a valve connected to the instrument inlet. After desorption the valve is switched in line with the pressurized solvent flow of the instrument and the entire volume of the desorption solution with dissolved analytes is introduced to the instrument.

Modification for Efficient LC Quantification

Figure 13:
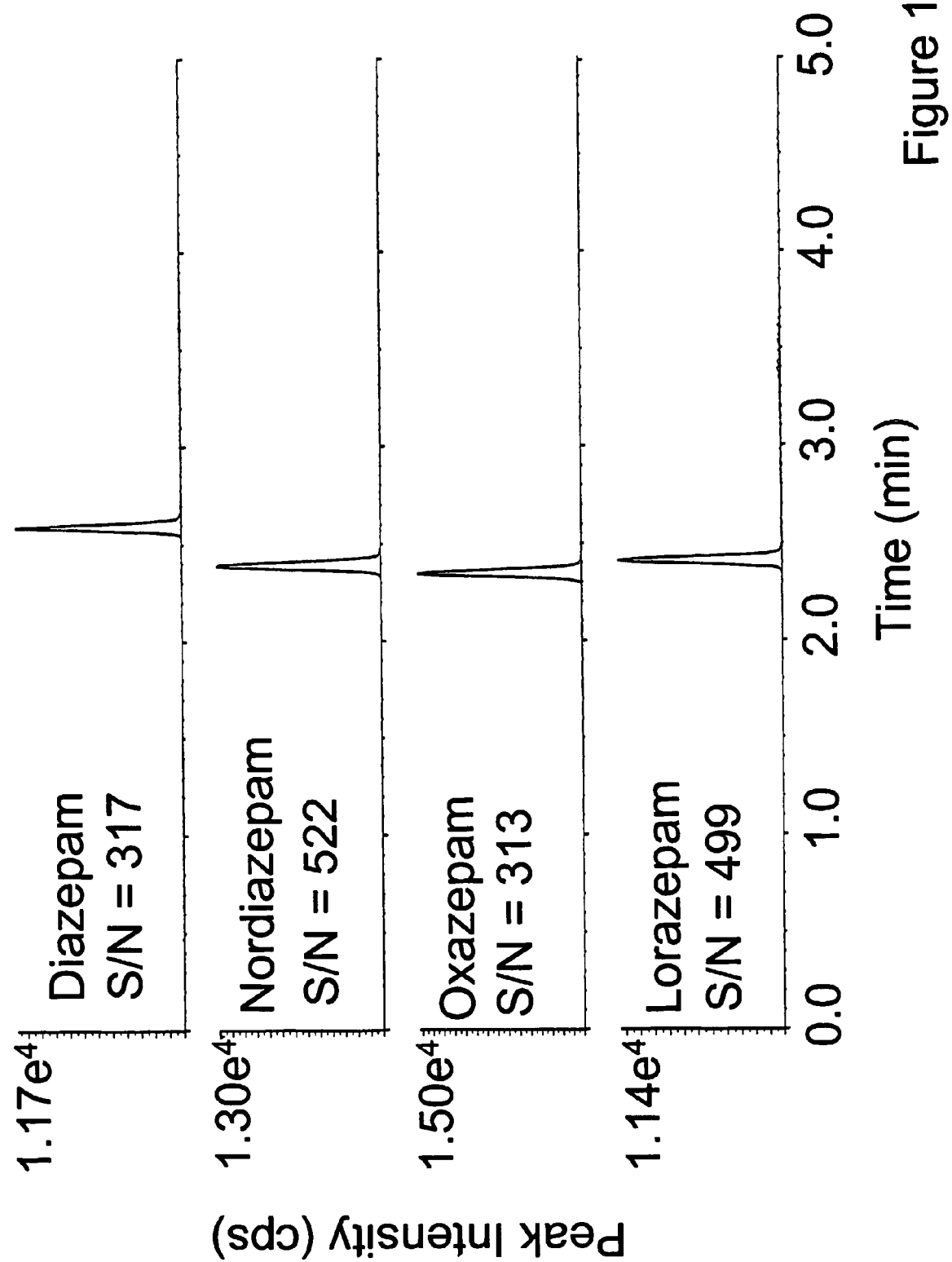
FIG. 13 illustrates an example chromatograph obtained after LC/MS/MS quantification of device extraction from plasma.

The technique has been limited by the relatively large volume of the commercial desorption interface (100 µL). Because of the phase thickness of the commercial SPME devices for LC (ca. 50 µL) this large volume is required. If desorption volume is reduced a significant proportion of the analytes are not removed from the fibre. Carryovers in the range of 20% are common (depending on the specific analyte and desorption solvent used) as the volume of desorption solvent is reduced below 50 µL. These volumes, however, are too large for typical LC applications as injection volumes are in the 10-20 µL range, particularly for LC/MS applications. Large injection volumes in these analyses typically produce unacceptably broad chromatographic peaks and poor resolution. When only a small portion of the total desorption solvent is injected, inferior sensitivity results. One strength of device of the instant invention is the ability to introduce all of the extracted analyte to the instrument for quantification. This allows for maximal sensitivity. Fibres with significantly reduced phase thicknesses, such as the polypyrrole coated wire described for the pharmacokinetic analyses, may be efficiently desorbed in 10-20 µL of desorption solvent. The entire desorption volume may then be injected for quantification. The result is sharp, symmetrical peaks as are shown in FIG. 13, which may be accurately integrated and produce good chromatographic resolution.

The foregoing described the use of static desorption, but dynamic desorption of analytes is also of interest in certain applications. This is achieved by passing desorption solvent over the fibre during desorption. Because the fibre is continuously exposed to fresh desorption solvent, quantitative desorption is theoretically possible. The rate of desorption is governed by the rate of solvent flow over the fibre. Faster flow results in faster desorption. To achieve the fastest desorption possible and to avoid ending up with an overly large solvent injection plug, it is necessary that the inner diameter of the desorption chamber is as small as possible. When volumetric flow is constant, faster linear flow is achieved in a smaller diameter chamber. This results in a shorter desorption time and hence a minimized total desorption volume.

Automation of LC Quantification

While the reduced volume HPLC interface used to date allows for efficient transfer of analytes from the fibre to the instrument, the process is only partially automated. To date the introduction and removal of the probe wire to/from the interface must be performed manually for each injection.

Figure 14:
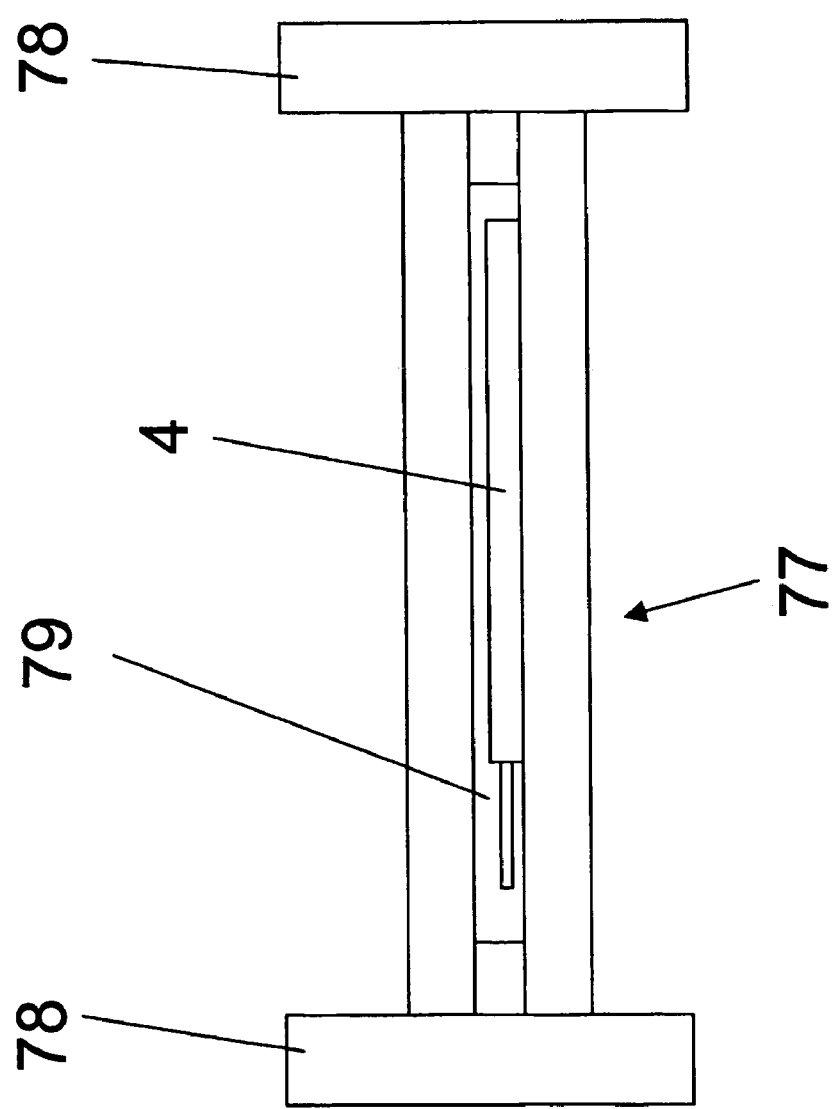
FIG. 14 shows a cartridge holding a fibre.

FIG. 14 illustrates a micro-cartridge 77, which contains coated piece of fibre in its small cavity 79 and sealed with plugs 78. The cavity 79 can be filled with desorption solvent. After extraction the coated piece of fibre containing the coating 4 is placed in a cavity 79 of the cartridge 77 for protection during storage and transport. Determination of extracted components can be performed in an automated instrument adopted for use with cartridges.

Interface for CE, Use of Electrokinetic Stacking

As discussed above, the device of the instant invention provides an ideal means for interfacing sampling and sample preparation to microanalytical instruments, particularly when devices much smaller than the commercially available SPME devices are employed. In capillary electrophoresis and related technologies, analytes are separated in a capillary typically 50 µm in diameter. This is too small for conventional syringe injection. Injection is typically by hydrodynamic or electrokinetic means. With hydrodynamic injection a sample is placed in the buffer reservoir associated with one end of the capillary. That end is then lifted above the opposite end by a prescribed amount for a prescribed time. The volume of sample entering the capillary may be calculated from the time, the elevation difference, the capillary diameter and the solution viscosity. The sample solution is then exchanged for running buffer solution prior to applying the separation voltage. While simple, the technique suffers from inaccuracies in injection volume and poor reproducibility from one analysis to the next. With electrokinetic injection a sample is again placed in the buffer reservoir associated with one end of the capillary. An injection voltage is applied across the reservoir and capillary and analytes in solution move into the capillary by electromotive force. Once sufficient material has been injected the voltage is removed and the sample solution is again exchanged for running buffer solution prior to applying the separation voltage. This method suffers from inaccuracy in injections due to the variation in electrophoretic mobility between analytes. This results in different amounts of the different compounds present being injected. A small diameter fibre with extracted analytes may be introduced directly inside a CE separation capillary filled with running buffer (Whang, C. W., Pawliszyn, J. Anal. Commun., 1998, 35, 353-356). This allows for accurate, quantitative introduction of analytes for separation.

As an improvement to this technique for CE analysis, by carefully matching the outer diameter of the fibre and the inner diameter of the separation capillary, a stacking of analytes occurs prior to separation results. This allows for much superior resolution. Electrophoretic velocity is inversely proportional to the cross-sectional area inside the separation capillary. When this area is reduced, increased velocity results because of an increase in electric field gradient. When a fibre is introduced inside a CE capillary, the space between the fibre and the capillary wall has a much smaller cross-sectional area than the space after the fibre where only buffer is present in the capillary. When a fibre is present and separation voltage applied, the analytes move out of the fibre and along the restricted channel quite quickly. When they reach the area of open capillary mobility drops significantly and the analytes are concentrated in a narrow band. During separation a higher resolution is achieved than would otherwise be possible.

Figure 15:
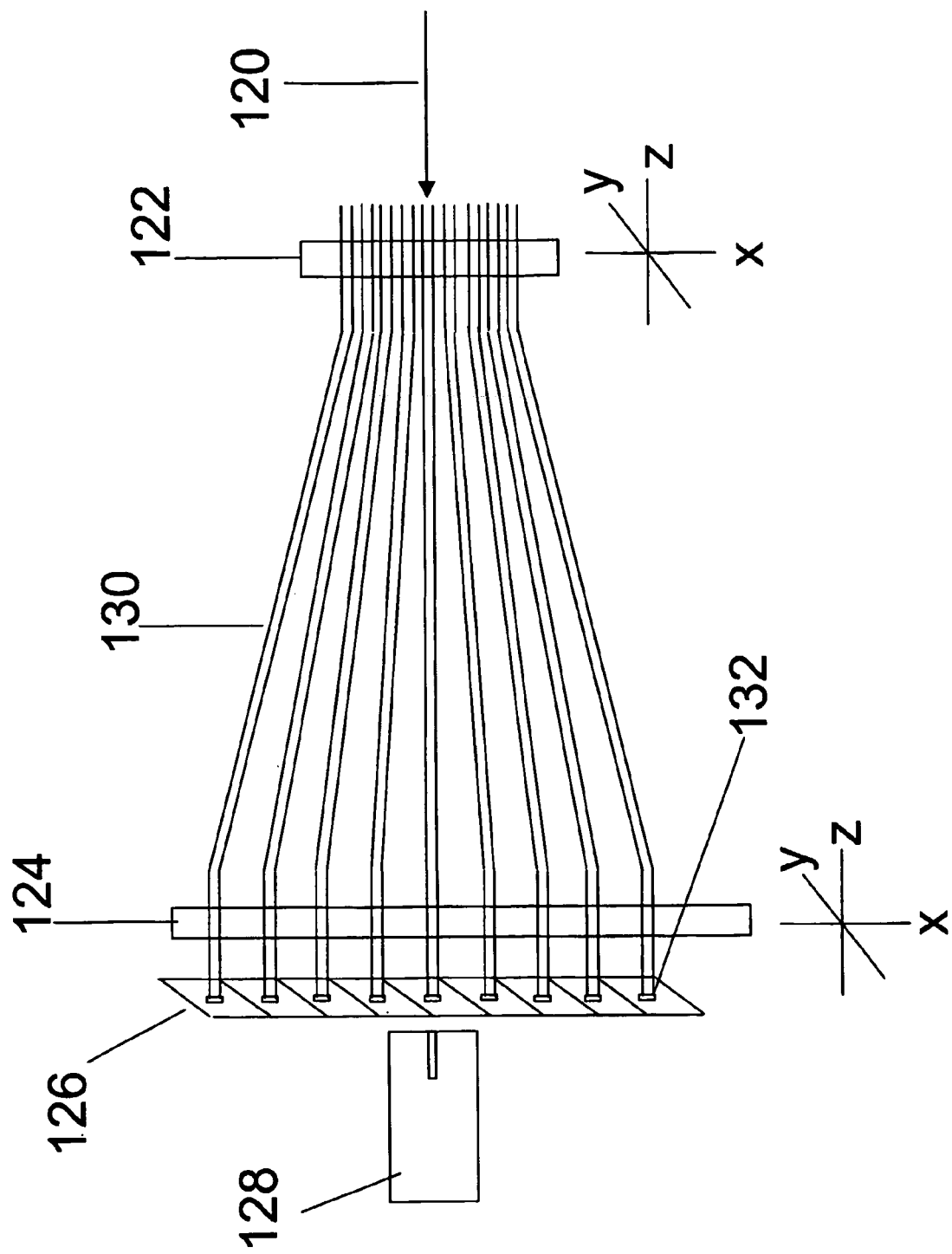
FIG. 15 is a schematic of batch process for parallel extraction and multiple MALDI desorption with positioning devices at both laser source and desorption ends of fibres.

FIG. 15 illustrates x-y-z positioning device for use with a fibre bundle. Individual fibres may be positioned precisely in the separation capillary prior to desorption. In this case the extraction phase would be coated on more than just the very tip of the fibre, as is shown in FIG. 15 (132) and desorption would be accomplished by applying an appropriate electric potential rather than by laser pulsing.

Direct Introduction to MS Through Nanospray Nebulizer

In some instances it is not necessary to chromatographically separate extracted analytes prior to quantification. This is the case where the fibre has very high selectivity such that only the analyte of interest is extracted with no interfering substances. It is also true where mass spectrometry is used for detection/quantification and components are separated by mass rather than by time prior to quantification. For MS applications it is possible to place the fibre directly into a nebulizer needle in an electrospray ionization source.

Figure 16:
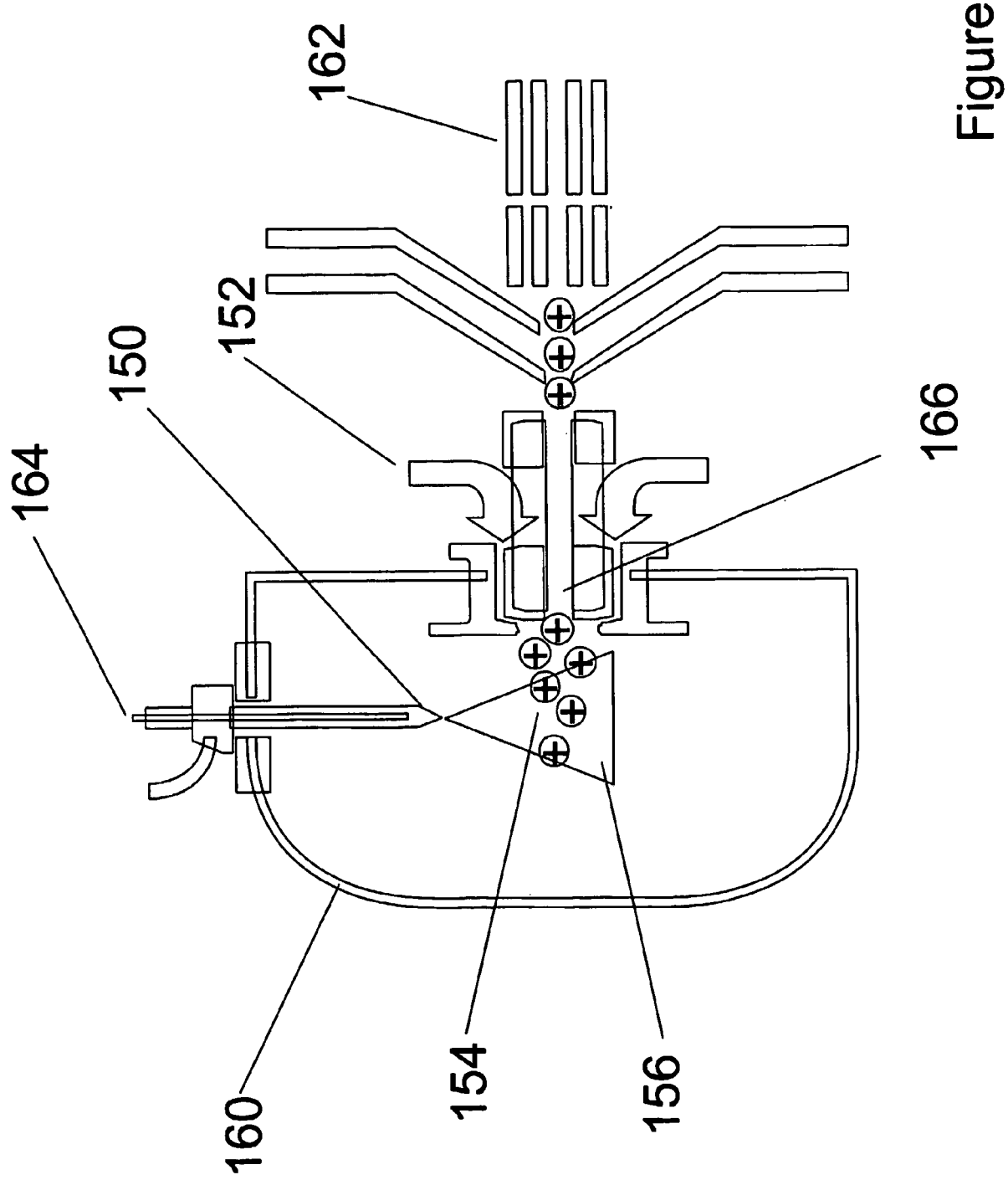
FIG. 16 is a schematic of the inventive device used with nanospray nebulizer and ESI MS.

FIG. 16 describes this process schematically. Solvent flowing through the nebulizer 150 efficiently desorbs analytes from the fibre 164 prior to being nebulized and sprayed in a plume 156 in a mass spectrometer atmospheric pressure ionization source 160. Ionization is then accomplished by standard ESI with MS detection, ie. droplets in the plume 156 are dried and reduced in size by hot gas flow 152 until ions 154 form in the vicinity of the orifice 166. These then pass into the mass analyzer 162 in the instrument.

Application to MALDI Analysis

Matrix-assisted laser desorption/ionization (MALDI) is a technique for ionization of molecules using a laser as the energy source. As a very soft ionization method, MALDI yields primarily the singly charged protonated molecule which are then conveniently quantified by either ion mobility spectrometry or time of flight mass spectrometry. This feature has made MALDI a widespread ionization tool for high molecular weight, nonvolatile and thermally labile analytes. MALDI has enabled the routine determination of large bimolecular such as peptides and proteins (P E. Jackson, P F. Scholl, and J D. Groopman, *Molecular Medicine Today*, 2000, 6, 271.)

The embodiment of the invention wherein the inventive fibre device is coupled to MALDI advantageously allows a combination of sample extraction with the ionization procedure on the very tip of a fused silica optical fibre for bimolecular analysis. The sample end of the fibre was coated for the extraction of peptides and/or proteins in a matrix solution. In the case of enkephalin and substance P the matrix used was alpha-cyano-4-hydroxy cinnaminic acid. The optical fibre thus served as the sample extraction surface, the support for the sample plus matrix, and the optical pipe to transfer the laser energy from the laser to the sample. Laser energy was transferred through the other end of the optic fibre to ionize and desorb the biomolecules for subsequent analysis. This fibre/MALDI combination was coupled with an ion mobility spectrometer and a tandem quadrupole/time-of-flight mass spectrometer (in separate experiments) for the detection of the MALDI signal.

Figure 17:
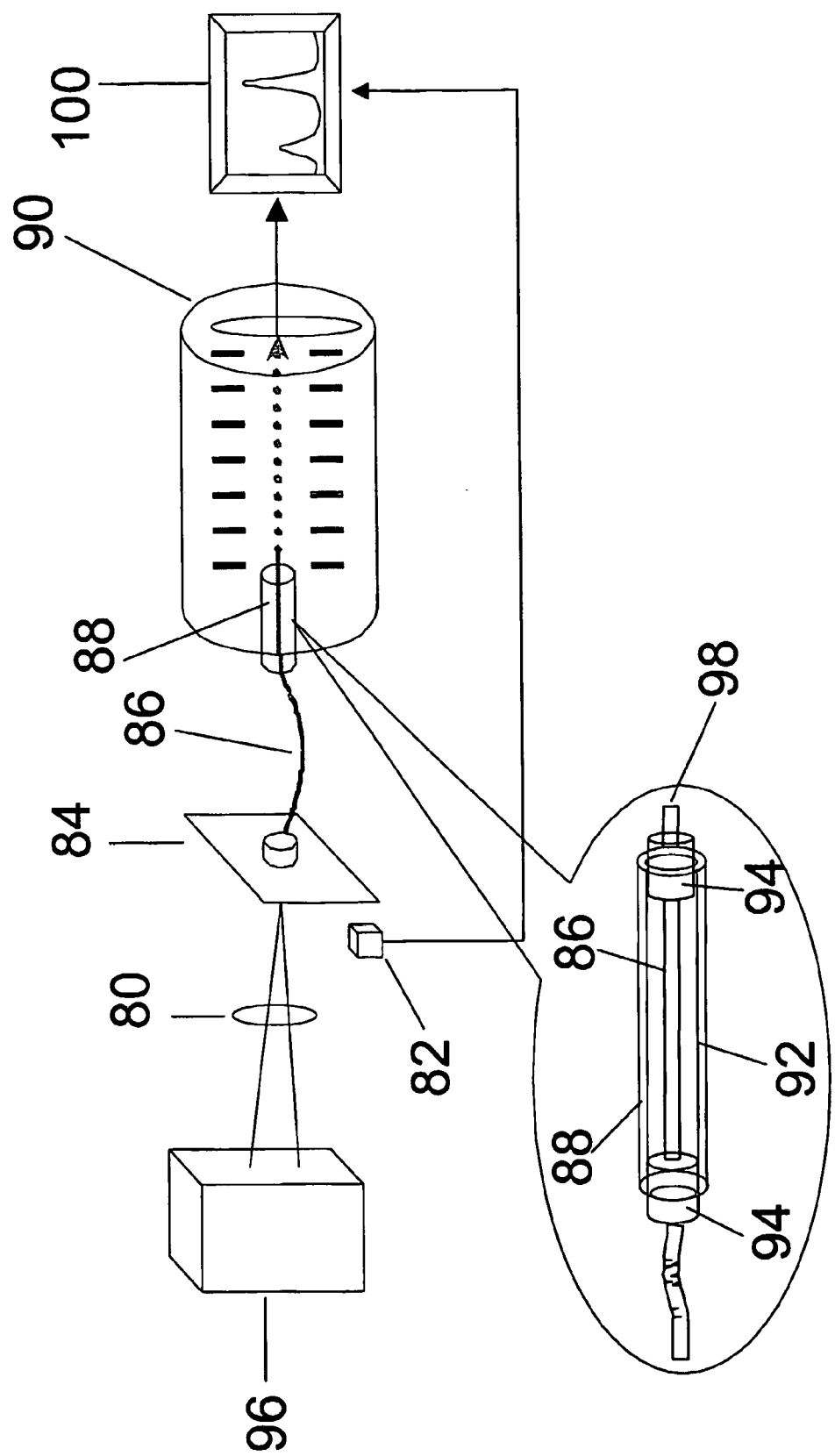
FIG. 17 shows a schematic of fibre/MALDI-IMS system according to the invention.

FIG. 17 shows a schematic of the fibre/MALDI-IMS interface and instrument. This consists of a laser source 96 and focusing lens 80, which focuses the laser light onto the uncoated end of the fibre, held in an x-y-z positioning array 84. The array movement may be manual or automated. The fibre 86 transmits light from the source to the x-y-z positionable inlet 88 of the mass analyser 90, which in this case was an ion mobility spectrometer. In the inlet 88 the coated end of the fibre 86 is held in place by two silicone septa 94 and a section of support tubing 92. Only the very tip 98 of the fibre is coated with extraction phase. A photosensitive diode 82 is positioned at the laser source 84 to sense the desorption laser pulse and initiate data collection 100.

Figure 18:
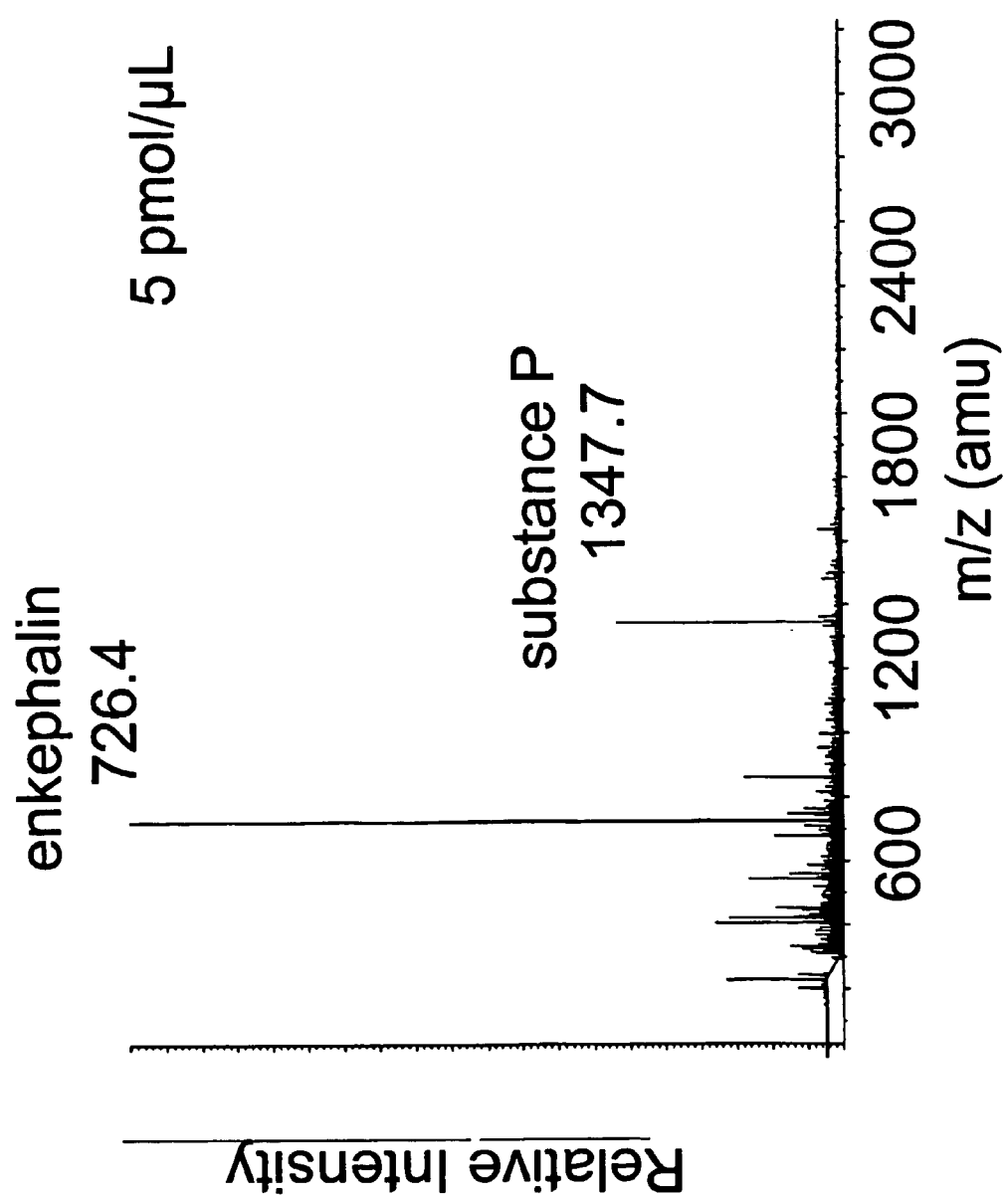
FIG. 18 illustrates an exemplary mass spectrum obtained from a fibre/MALDI-IMS system according to the invention

FIG. 18 shows the ion mobility mass spectrum of enkephalin and substance P were obtained using this system.

One advantage of the MALDI/IMS interface is that the MALDI source is operated at ambient pressure instead of high vacuum, as it is in conventional MALDI/TOF mass spectrometery. Also, loss of sample delivered to the drift tube is negligible at ambient pressure and it has been reported recently that atmospheric pressure MALDI produces a generally uniform ion cloud at atmospheric pressure. The ionization process is even softer than that of the conventional high vacuum MALDI and is capable of producing protonated molecular ions for small proteins. This is convenient for the MALDI analysis of macromolecules because of the relative absence of metastable fragmentation and discrimination in the ionization process compared to conventional vacuum MALDI. The most promising advantage of this ambient interface is the possibility of interchangeably using the same instrument for both electrospray and MALDI sample introduction.

Figure 19:
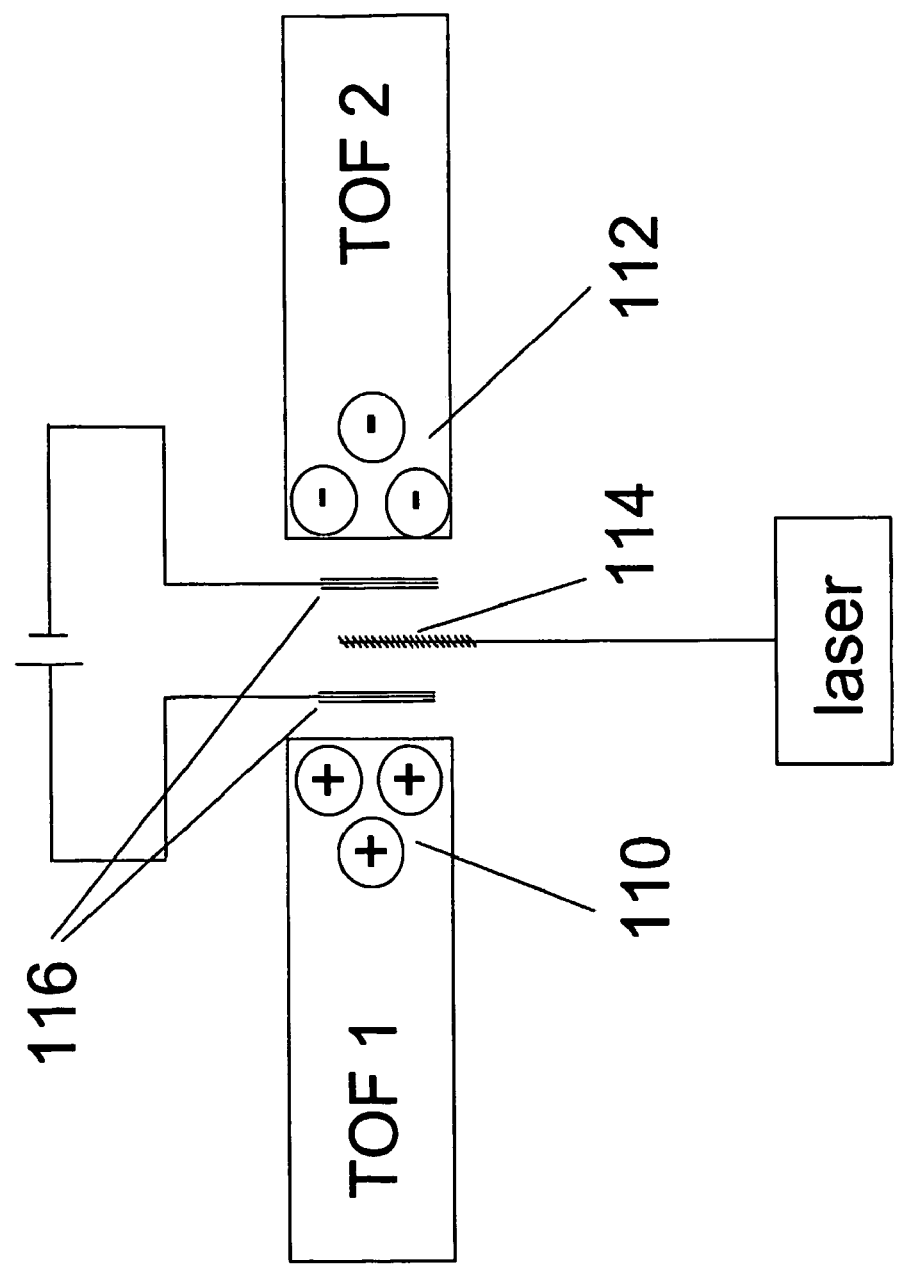
FIG. 19 is a schematic of a fibre/MALDI source.

FIG. 19 shows a schematic of the laser desorption interface an ion formation. In this case two time of flight mass spectrometers (TOF) are used, one to sample positive ions 110 and the other to sample negative ions 112. A laser pulse initiates desorption from the extraction phase 114 and polarized plates 116 accelerate the appropriate ions into the appropriate mass analyzer.

Though MALDI has enabled the routine determination of large bimolecules such as peptides and proteins, it has always been great interest to develop quantitative MALDI analysis. For quantitative work with conventional MALDI analysis, the laser beam is scanned cross the sample area on the target plate, and each sample spot is irradiated with multiple laser shots until a striking decrease in signal detection is observed which indicates the removal of most of the sample loaded on this particular spot. Therefore, tens to hundreds of laser shots must be fired to finish the scanning process, and the final spectrum is typically a sum or an average of all the spectra obtained from each laser shot. This sampling process will lead to the unavoidable poor shot-to-shot and spot-to-spot sample reproducibility, and has been considered as the fundamental limitation for method quantification in MALDI analysis.

The combination of the inventive device with MALDI has technically solved the above problem as it combines sample extraction with the ionization procedure on the tip of a fused silica optical fibre. The optical fibre thus served as the sample extraction surface, the support for the sample plus matrix, and the optical pipe to transfer the laser energy from the laser to the sample. Since the sample was loaded directly on the fibre tip, so the sample size was identical to that of the laser irradiance area and there existed no spot-to-spot desorption difference. In addition, due to the multiple reflections inside the fibre, the primary laser profile is converted into a homogeneous intensity profile at the sample end fibre surface. This means that laser emission is homogeneous through the fibre tip surface. The method was developed as to accomplish all sample desorption that was extracted on fibre tip with a single laser shot. As long as this situation could be satisfied, the spot-to-spot and shot-to-shot spectral disparity would also be minimized. In this way it dramatically improved the quantification aspect of MALDI as well as saved large amount of analytical time and analyte consumed. To explore the quantitative aspects of the fibre/MALDI method TOAB was selected as the analyte compound and all experiments were performed in the matrix DHB. The fibre/MALDI-IMS system described in FIG. 17 was used for quantification.

In the extraction step of the previous experiments, the tip of the fibre/MALDI fibre was dipped into the solution containing both sample and matrix. For this pre-mixed extraction method, the analyte to matrix ratio was pre-optimized and fixed for the best performance and this is almost impossible for the detection of analyte in real samples of unknown concentrations. Meanwhile, due to the very small capacity of the extraction phase, there exists a competition between the analyte and matrix that causes a further limitation for the amount of analyte that can be extracted. A more practical way is to load the matrix in a second step after sample extraction. Spray method with a nebulizer is an ideal candidate for this purpose as it forms very fine solution drops smaller than 100 nm. After sample extraction, matrix solution is loaded with a nebulizer. The fog like matrix drops would help to form more uniform cocrystalline on the fibre tip surface. The amount of matrix loaded on the fibre or matrix to analyte ratio could be easily adjusted by varying the concentration of the matrix solution and the spray time.

Example 2 describes use of a MALDI/IMS interface which is associated with reduced noise. Reduced noise, though convenient, is not necessary. Thus, careful alignment of the laser with the sample surface is optional, as the fibre itself can accomplish this. As an alternative however, it would still be feasible to conduct a conventional MALDI analysis where the laser is directed at the surface of the fibre. This would allow devices to be constructed from non-light conducting fibres, and would eliminate the need to optically couple the device and the laser prior to analysis.

Multiplexing for Parallel Extraction and Quantification

The inventive device described lends itself to parallelization in both the sampling and quantification steps, due to both its cylindrical geometry and simplification of the analytical process.

FIG. 15 illustrates that parallel sampling could be accomplished by bundling multiple fibres, with the same or different coatings, to either probe multiple samples at once or to probe a single sample for multiple analytes. The bundle of fibres could also be used to provide efficient stirring during extraction. The extraction can be from multi-well autosampler plate, each well containing a different sample is extracted by a single fibre facilitating highly parallel determinations. The bundled extraction device could be employed for quantification by the MALDI process described above. The bundle could be multiplexed to a light source, and each individual probe irradiated in sequence by targeting the source at each individual fibre in succession. Simultaneously the sample end of each fibre would be positioned at the instrument for analysis. As shown in FIG. 15, a laser source 120 is irradiated in sequence onto each fibre in a fibre bundle 130 by means of a positioning device 122. The sample ends of the fibres in the bundle are directed into an extraction/desorption mesh 126. In this case only the tips of the fibres are coated with extraction phase 132 as this is the surface that is irradiated by the laser light. The sample end is positionable by means of a second positioning device 124. As each fibre is ready to be desorbed, it is positioned by the positioning device 124 at the sampling orifice of the mass analyzer 128 and the laser 120 is fired to intimate desorption.

Alternatively the probe bundle could be desorbed simultaneously into individual solvent desorption wells, with quantification by LC/MS.

The combination of fiber MALDI analysis with multiwell plates may also involve a positioning device to allow proper placement of the distal end of each coated fibre within a small opening of each well, so as to submerge the extraction phase. This approach requires design of a relatively small and accurate positioning device, to accommodate the large number of wells in a single high density multiwell plate. The technology now allows for over 1,000 wells to reside on one plate. Other introduction techniques may be used to introduce a sample or fibre into a well, specifically by using micromachined microfluidic systems where many microfluidic channels can be placed in one microfluid device to accommodate each fibre. This can be performed in combination with nanospray introduction to MS, where all fibres are desorbed in parallel in a microstructure, and subsequently each desorbed solution is introduced to MS in sequence.

EXAMPLE 1

Preparation of Polypyrrole Coating on Stainless Steel Wires and Use in a Biological System Stainless steel wires (grade T-304V, 0.005") were from Small Parts Inc. (Miami Lakes, Fla.). Lithium perchlorate (95%) and pyrrole (98%) were from Sigma/Aldrich (Mississauga, ON). Pyrrole was used as received for one month after opening, was stored refrigerated and the bottle was layered with nitrogen after each use. Polypyrrole (PPY) films were deposited onto the supporting electrode surface (stainless steel wire) by anodic oxidation of the pyrrole monomer in the presence of an aqueous electrolyte solution (counter ion). A potentiostat/galvanostat (Model 273, EG&G Princeton Applied Research) was used for the electrodeposition. The last 15 mm of the wires were coated potentiostatically at 0.8 V for 20 minutes. The placement of a silicon septum 15 mm from the end of the wire allowed for accurate control of coating length. The coating solution used was pyrrole (0.1M) and lithium perchlorate (0.1M) in water and was prepared fresh daily. Coating was performed in a custom designed 50 mL flow-through glass compartment. Coating solution was pumped through the compartment continuously to allow for one complete change of solution during each deposition (50 mL/20 min.). The stainless steel wires were cut into 10.7 cm sections with a razor blade and 2-4 cm at the end to be coated was etched with 400 grit silicon carbide polishing paper. Wires were then sonicated in acetone until required to prevent accumulation of oxides or other contaminants on the wire surface. Immediately before use the wires were rinsed briefly with water and were installed as the working electrode. The counter electrode consisted of a ca. 10 cm section of platinum wire (0.75 mm OD) formed into a coil of about 1.5 cm diameter. The stainless steel wire was placed into the coating solution in the centre of this coil. A calomel reference electrode was used. The polypyrrole coating thickness was estimated to be<10 µm thick. Prepared probes were then placed into vials with sufficient buffer to cover the extraction phase and autoclaved for sterilization.

Wires prepared as described above were characterized in a series of in vitro experiments. Benzodiazepine standards (1 mg/mL in methanol) were purchased from Cerilliant (Austin, Tex.). These were diluted in methanol to prepare mixtures of various concentrations for use in sample preparation and instrument calibration. Samples were prepared from buffer, dog plasma or dog blood and spiked with an appropriate amount of the analytes of interest. The device was placed directly into the sample contained in an appropriate polypropylene sample vial, for a certain period of time. After extraction the probe was rinsed briefly with a stream of water and either analysed immediately or allowed to dry prior to analysis. Drugs were stable in the extraction phase when stored dry at room temperature for at least 24 hours.

Figure 20:
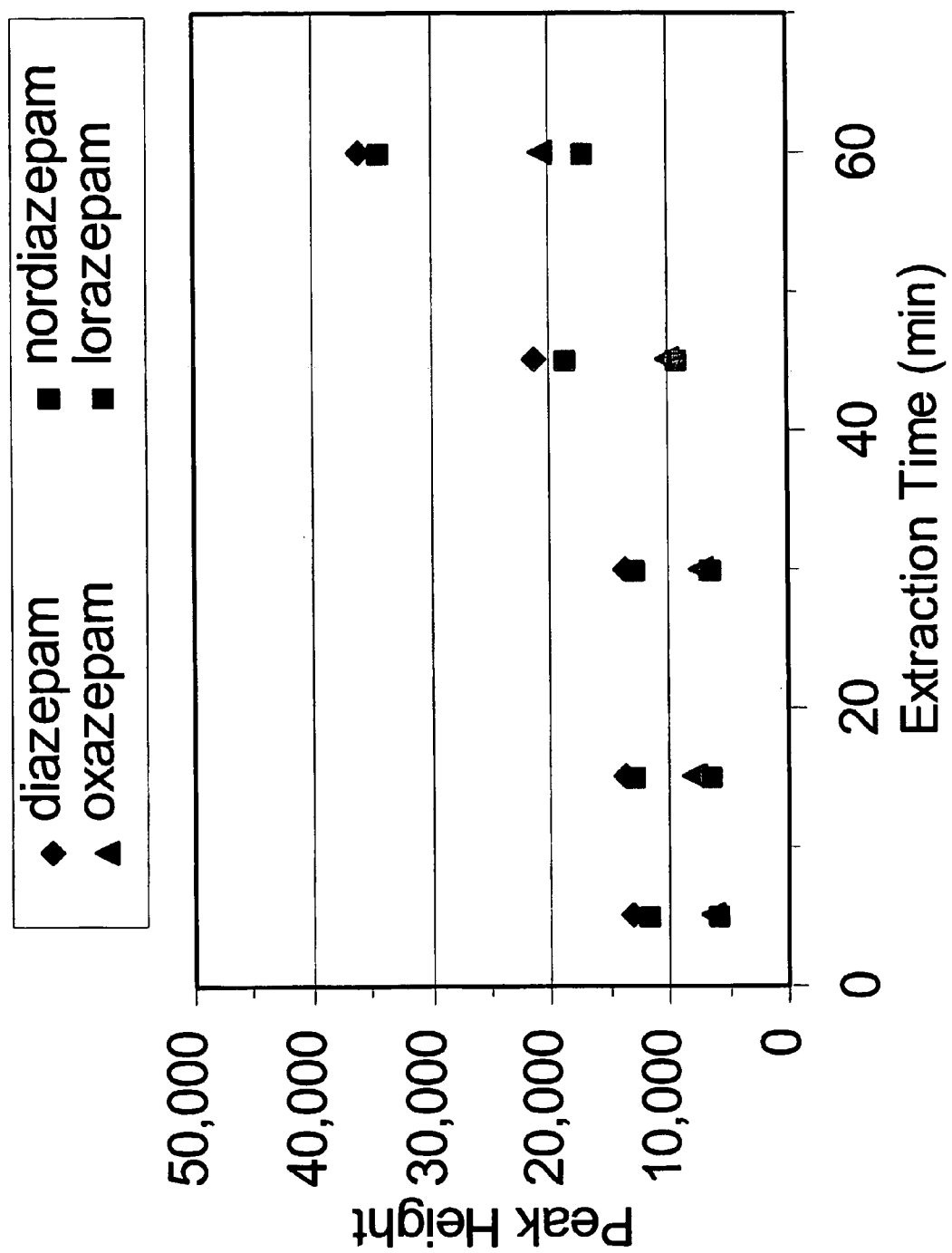
FIG. 20 shows extraction response versus time for standard devices.
Figure 21:
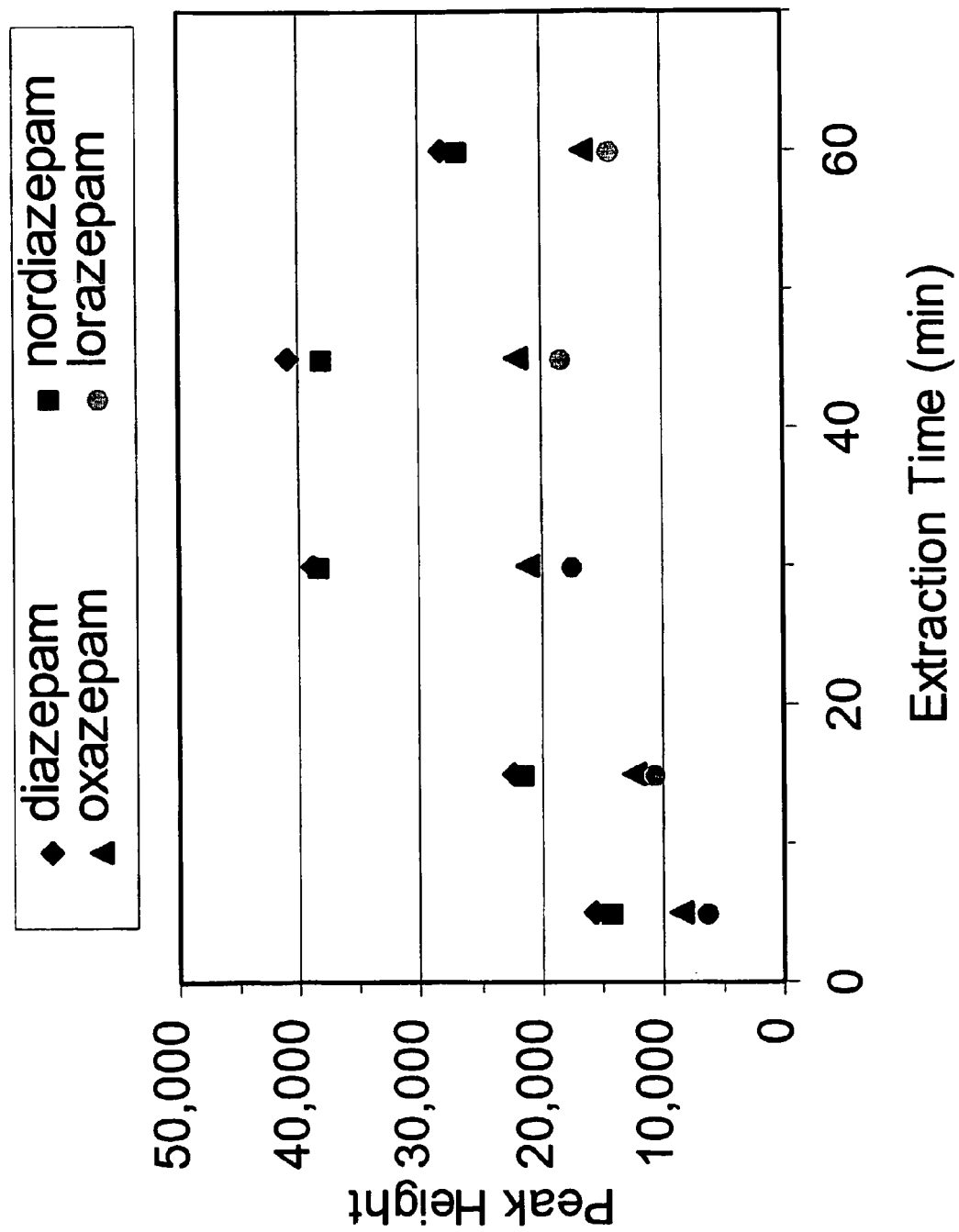
FIG. 21 shows extraction response versus time for preconditioned devices.

FIG. 20 and FIG. 21 show two alternatives for device response that may be achieved by this method. In FIG. 20 it can be seen that a fast initial equilibrium between the sample and native polypyrrole coated wires. After a longer period of time additional analyte is extracted as the polymer swells and exposes additional sites for extraction.

FIG. 21 shows that the polymer was preconditioned with methanol to provide a swelled polymer prior to extraction. The result the elimination of the initial lag time seen in FIG. 20 and an immediate increase in amount extracted with maximal extraction seen after 30 minutes when the analyte has diffused throughout the bulk of the polymer to access the additional sites exposed during swelling. This provides for additional sensitivity at the expense of a slower response time.

Figure 22:
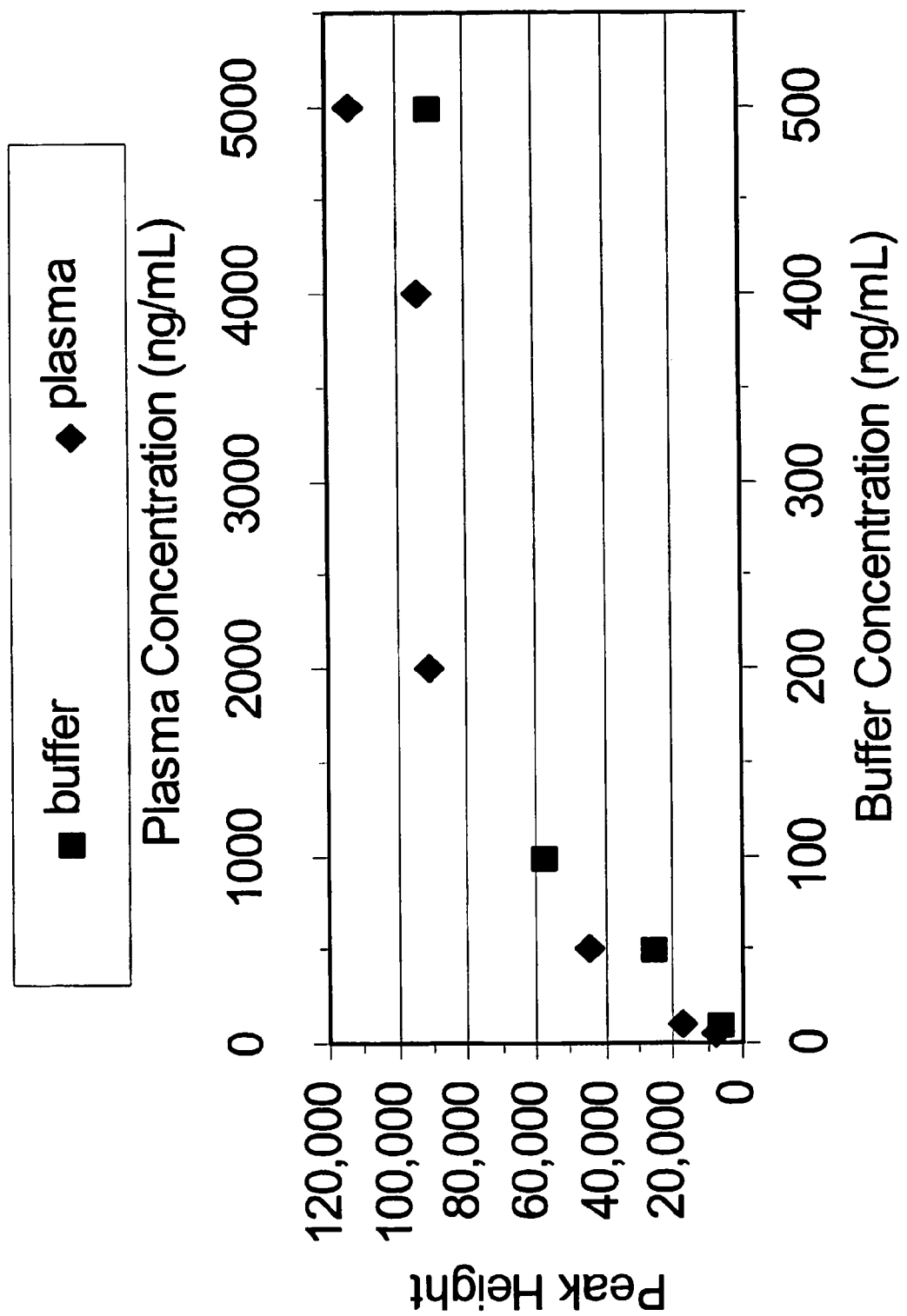
FIG. 22 provides a comparison of calibration in buffer and plasma, demonstration of linear response limit.
Figure 23:
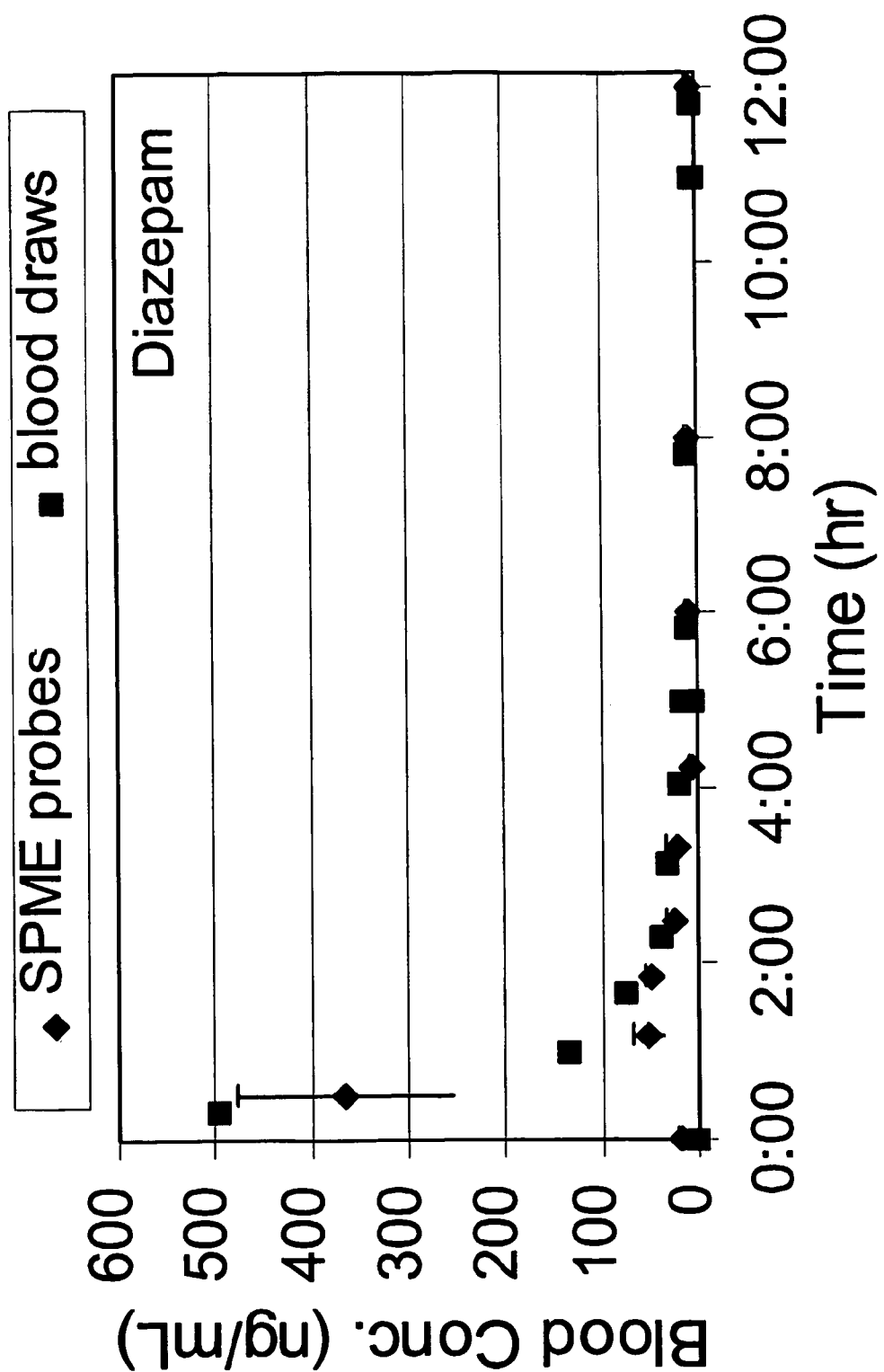
FIG. 23 illustrates an exemplary pharmacokinetic profile of diazepam.
Figure 24:
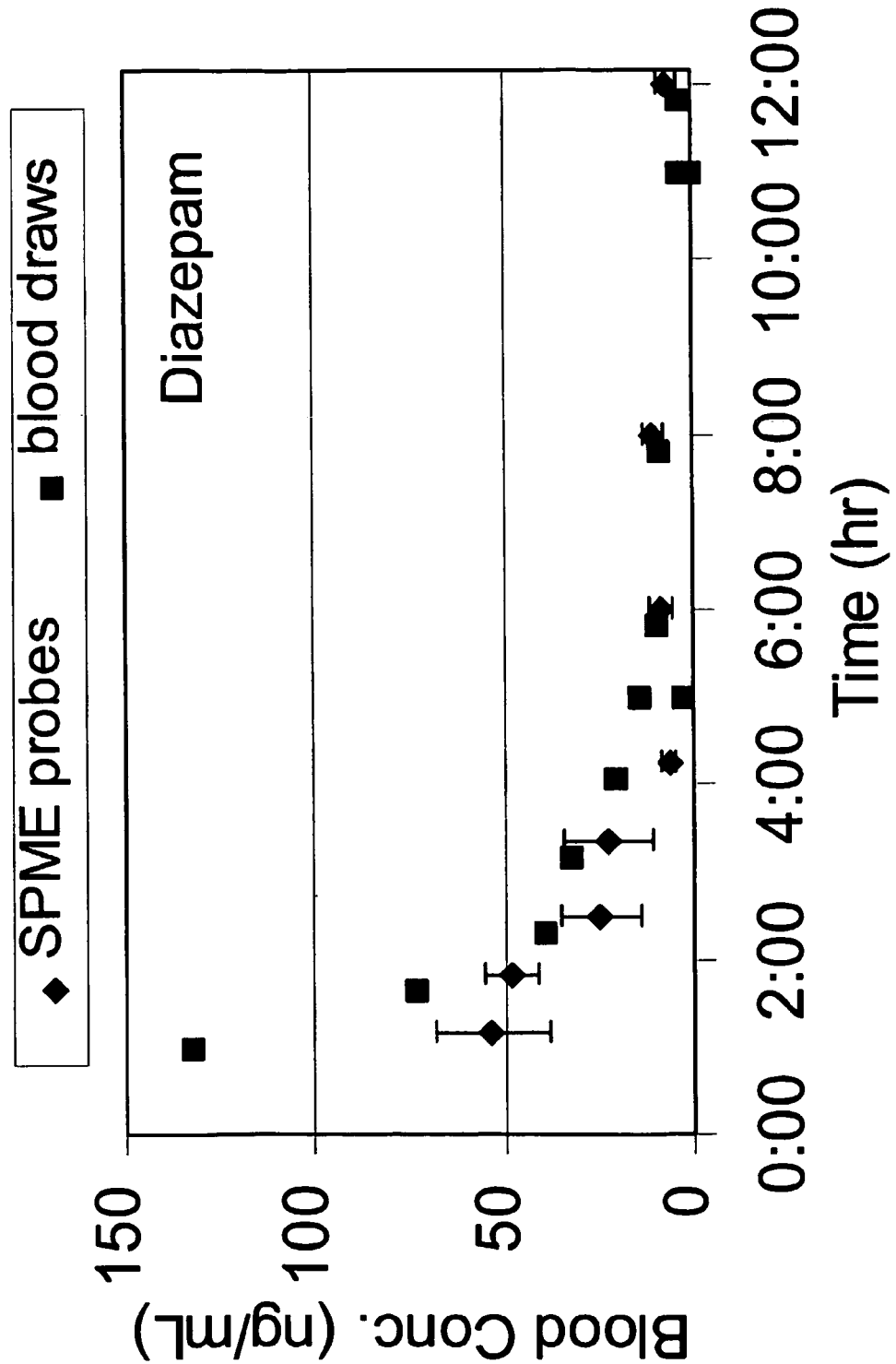
FIG. 24 illustrates an exemplary pharmacokinetic profile of diazepam, with an expanded y-axis.
Figure 25:
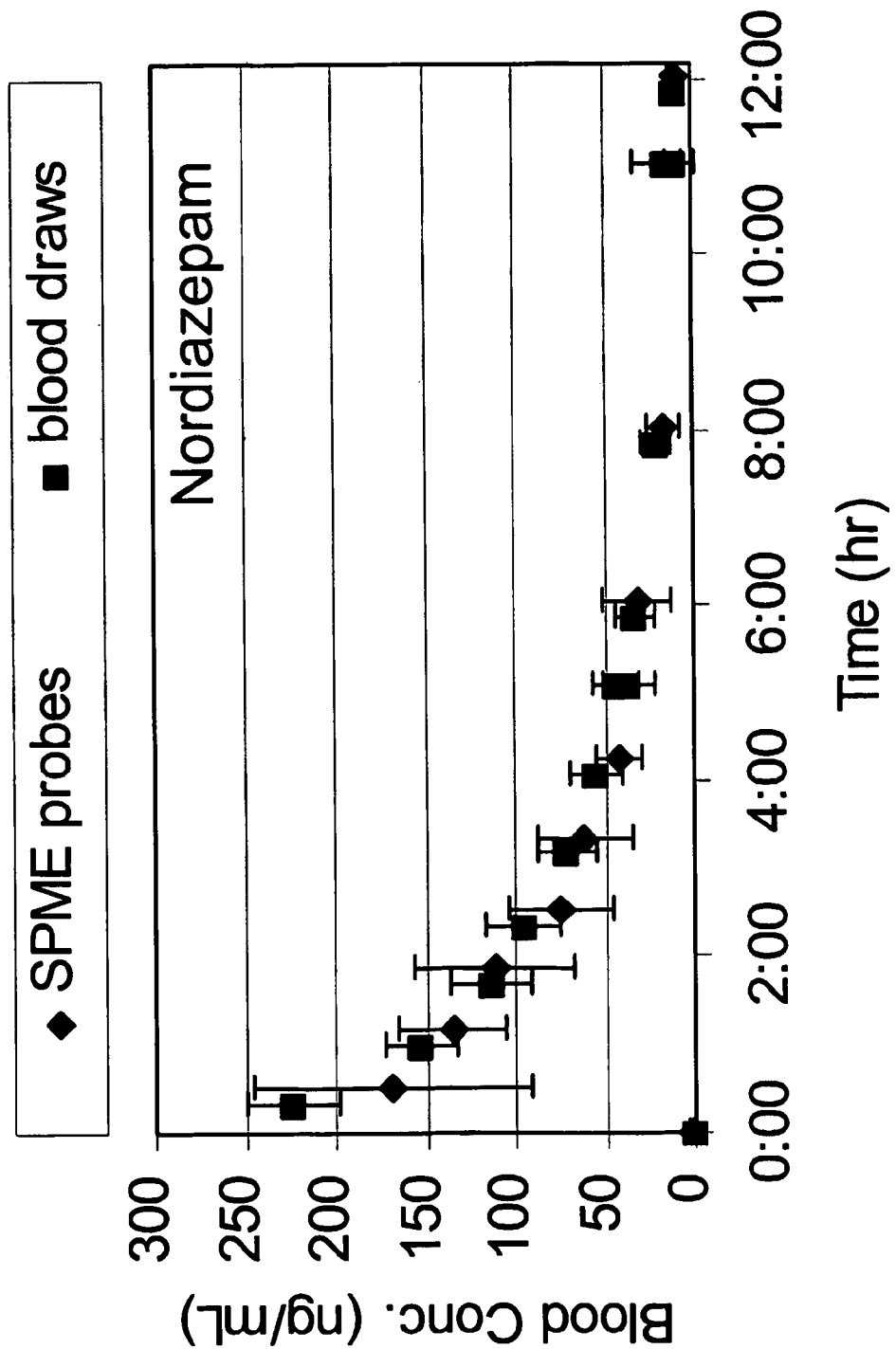
FIG. 25 illustrates and exemplary pharmacokinetic profile of nordiazepam.
Figure 26:
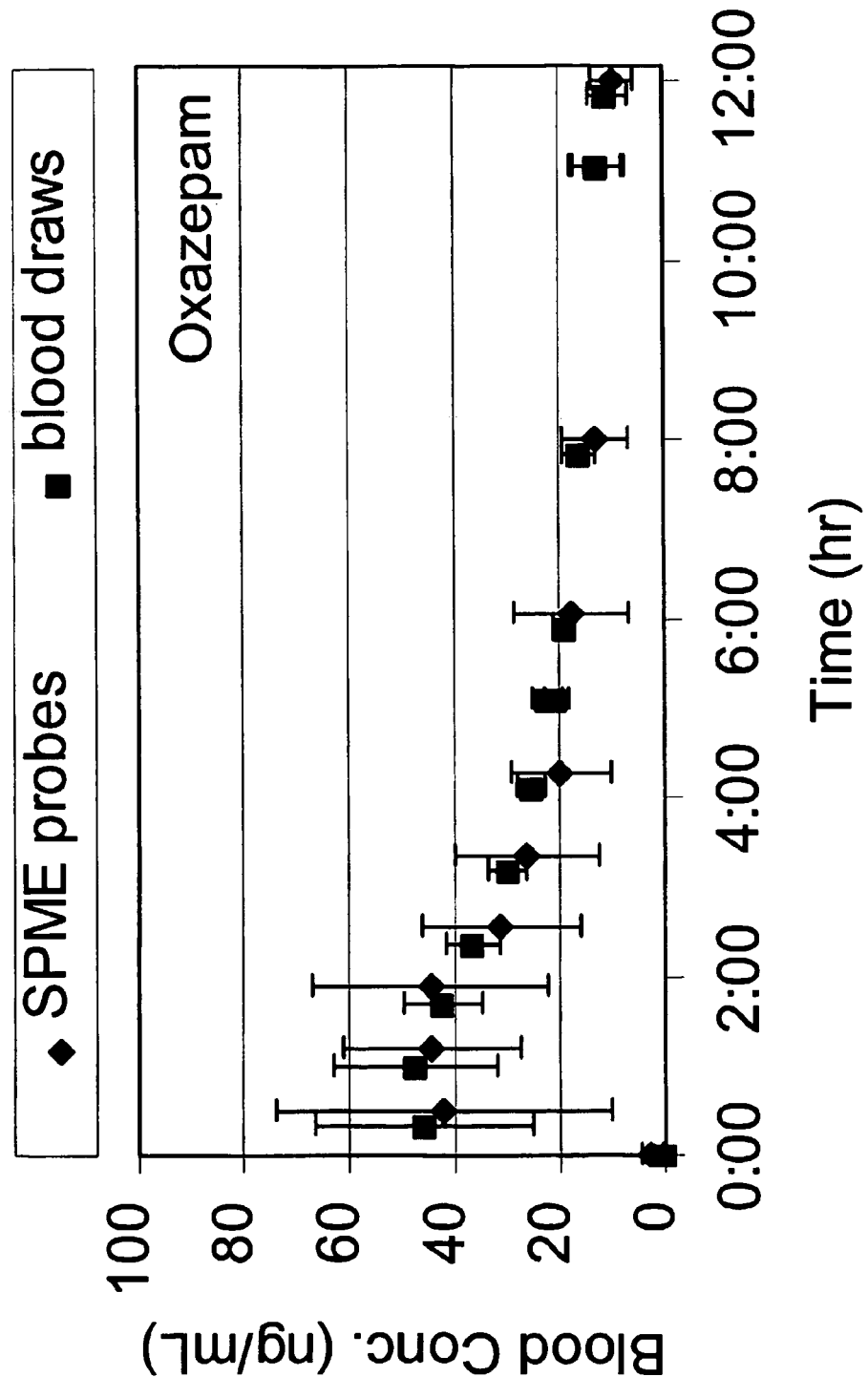
FIG. 26 illustrates an exemplary pharmacokinetic profile of oxazepam.

FIG. 22 shows the result of in vitro extraction calibrations from buffer and plasma. Because the device will only extract unbound drug and because the drugs under study are ca. 90% bound to protein, the plasma concentrations tested were 10x higher than the buffer concentrations. In buffer 100% of drug is free and 0% is bound to protein as no protein is present. In plasma, it is expected that 10% or less of the drug will be free. FIG. 22 demonstrates that the linear range attained is similar in buffer and plasma, based on free drug concentration. The figure also demonstrates that polymer extraction reaches maximal capacity in a solution with 100-200 ng/mL free drug.

After extraction (either in vivo or in vitro) the compounds on the device are desorbed in a small volume (10-20 μL) of desorption solvent, 75% methanol in this case. Maximal desorption is seen in as little as 20 sec. All or a portion of the desorption solvent is injected to an analytical instrument for analysis. This may be accomplished either on-line in a dedicated injection interface that takes the place of the regular injection port on a LC, or off-line in a small desorption chamber, followed by standard syringe injection of the desorption solvent by a commercial autosampler.

Figure 12:
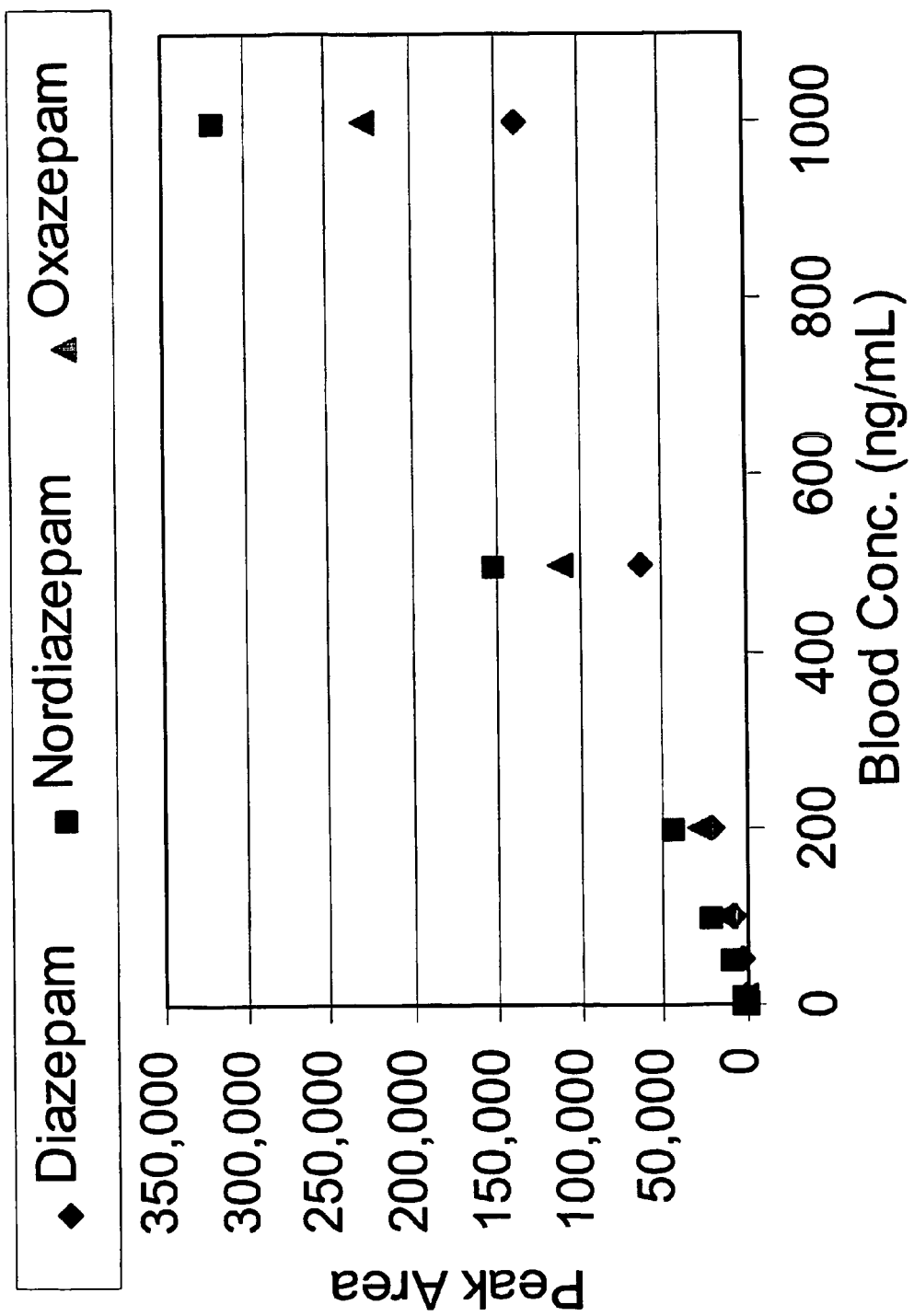
FIG. 12 illustrates calibration in whole blood used to calibrate device response.

FIG. 12 presents the results of a calibration from whole blood treated with an anticoagulant. The figure demonstrates good linearity in extraction over the range of total (bound plus free) drug shown.

FIG. 13 shows a chromatogram obtained after extraction of drugs spiked at 100 ng/mL from dog plasma, demonstrating the good chromatographic peak shape obtainable by the method. In this case the injection volume was ca. 11 μL, using the desorption solvent described above.

FIGS. 23 to 26 show the results of the use of the device by the catheter sampling method described above, for a pharmacokinetic study in dogs. In this case dogs were dosed with diazepam at time 0:00. Multiple samplings were performed from a catheter over the ensuing 12 hours. Calibration was by comparison to results from an external calibration in whole blood similar to that shown in FIG. 12. Also shown is a comparison to results obtained by multiple blood draws over the same time period, with conventional sample preparation and analysis as described in the description of the prior art. These results demonstrate that the device is useful for the application described and that the method described produces results in good agreement with devices and methods using invasive prior art sampling techniques.

Table 1 shows the limits of detection achieved in buffer and whole blood for a "probe" formed according to the invention. As can be seen from these data, the device and method allow an extremely sensitive detection of the analytes of interest, in this case: diazepam, nordiazepam and oxazepam.

TABLE 1

Limits of Detection Achieved in Buffer and Whole Blood

| Compound | Linear Range | detection limit (S/N = 3) ng/mL | slope | linear correlation ($r^2$) |
| --- | --- | --- | --- | --- |
| SPME probe calibration from whole blood | | | | |
| Diazepam | 1-1000 ng/mL | 7.1 | 215 | 0.999 |
| Nordiazepam | 1-1000 ng/mL | 3.1 | 328 | 0.994 |
| Oxazepam | 1-1000 ng/mL | 2.7 | 258 | 0.996 |
| SPME probe calibration from buffer | | | | |
| Diazepam | 10-100 ng/mL | 0.43 | 306 | 0.999 |
| Nordiazepam | 10-100 ng/mL | 0.24 | 281 | 0.998 |
| Oxazepam | 10-100 ng/mL | 0.35 | 169 | 0.995 |

EXAMPLE 2

MALDI Analysis

In this Example, a medical aerosol compressor was used as the matrix sprayer, and 10 mg/mL matrix DHB solution was deposited into the nebulizer vial. After analyte extraction the fibre tip was placed 1.5 cm above the nebulizer vial, and by turning on the compressor very fine drops of the matrix DHB solution were formed and attached to the fibre tip. The 800 μm fibre was tested with the spray method for a 0.05 mg/mL TOAB sample solution. The times for matrix application were set at 45 seconds and 30 seconds, respectively, considering the lower analyte concentration. Two 3 minute air-dry times were applied before and after the spray of matrix.

Figure 27:
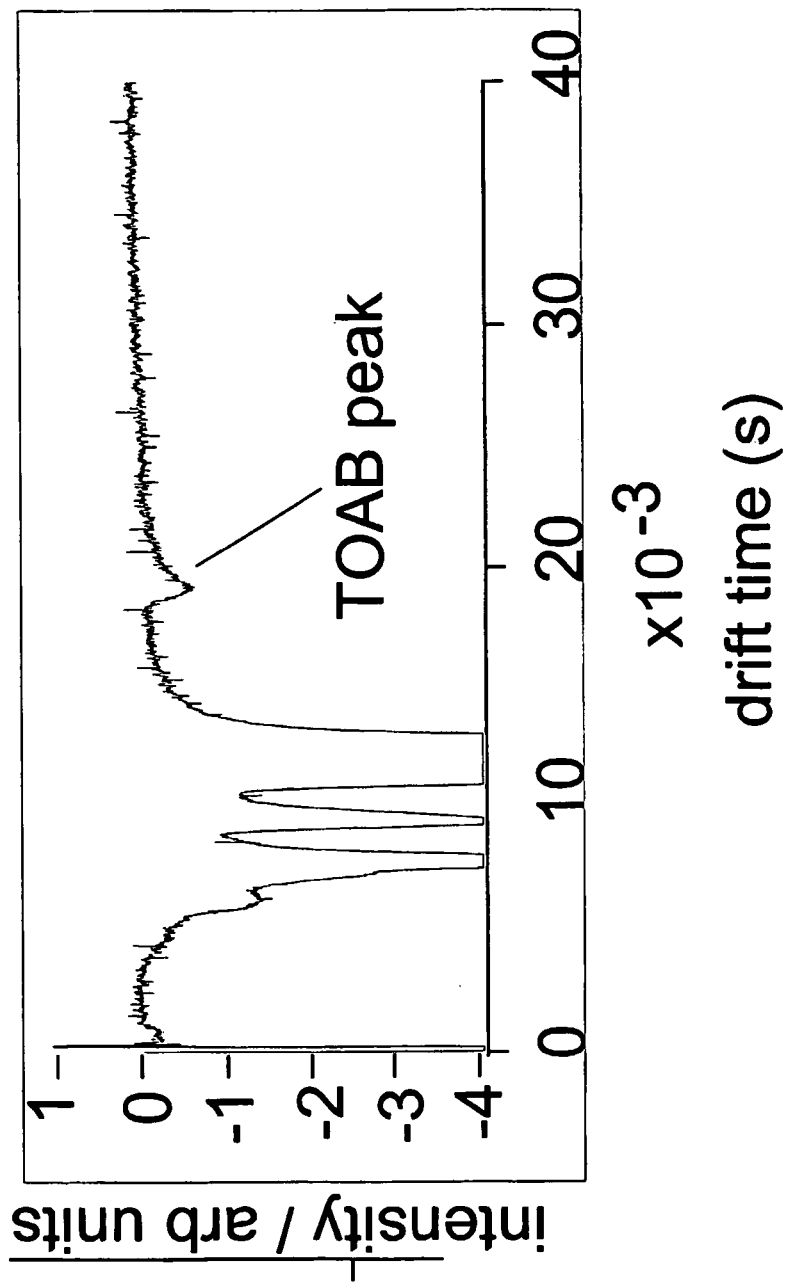
FIG. 27 shows an ion mobility spectrum obtained by matrix spray method at 0.05 mg/mL.

FIG. 27 shows an IMS spectrum from this analysis. The limit of detection was found to be 0.02 mg/mL with S/N ~2. This level is 10 times lower than the previous 0.2 mg/mL established by the 400 μm fibre using the pre-mixed method. The sensitivity has been increased dramatically. This great improvement was attributed to the larger surface area as well as the spray method.

In the work described above the laser pulse was shot down the core of the fibre. In addition to the advantages associated with reduced noise as described above, this is convenient as it is not necessary to carefully align the laser with the sample surface. The fibre itself accomplishes this. As an alternative however, it would still be feasible to conduct more of a conventional MALDI analysis where the laser is directed at the surface of the fibre. This would allow probes to be constructed from non-light conducting fibres, and would eliminate the need to optically couple the probe and the laser prior to analysis.

EXAMPLE 3

On-Fiber and In-Needle Laboratory

In micromachined devices, controlling flow is not simple since it requires pumps or electroosmontic flow means. In addition it is quite difficult to mix analytes in the small channels. A more efficient approach is to do sample processing on the surface or in thin layers adjacent to the surface. The structures chosen in this Example are the outer surfaces of fibers. Alternatively, the inside surface of a tube fiber could be used. This Example makes use of a small fiber to demonstrate a convenient sampling method to collect analytes from small objects. In this work capillary electrophoresis with fluorescence detection has been used to facilitate detection of small amounts of analytes extracted by the fiber.

Chemicals and materials. 4-fluoro-7-nitro-2,1,3-benzoxadiazole (NBD-F) was purchased from Fluka (Sigma-Aldrich Canada Ltd., Oakville, Ontario). Brij 35® and all amino acids (glycine, L-phenylalanine, L-proline, L-glutamate and L-aspartate) were obtained from Sigma-Aldrich Canada Ltd. (Oakville, Ontario, Canada). Sodium borate was from Fisher Scientific (Nepean, Ontario, Canada). All of the solvents used were HPLC grade, filtered and degassed and all the aqueous samples were prepared with deionized water (NANOpure, Ultrapure water system). A manual SPME assembly and replaceable extraction fibers, coated with Carbowax-temprated resin (CW-TPR, 50 um) were purchased from Supelco (Canada).

Instrument. The high voltage power supply for the CE system was from Spellman High Voltage Electronics Cooperation, Plainview, N.Y., USA. The CE separation capillary and silica fibers were purchased from Polymicro Technologies LLC, Phoenix, Ariz., USA.

The fundamental components of the laser induced fluorescence detection (LIF) are the laser, focusing lens, objective lens, interference filter and photomultiplier tube. An Argon ion (Ar+) laser (~5 mW) was the excitation source. It provided an excitation wavelength of 488 nm (its maximum). The microscope objective lens (10×) and the low pass filter (530 nm) as an interference filter were from Melles Griot (Toronto, ON, Canada). The photomultiplier tube (PMT) and its socket including a high voltage power supply were purchased from Hamamatsu (R928 and C6271, Bridgewater, N.J., USA). In the design, the optical chopper and lock-in amplifier were used to enhance the signal indirectly. The optical chopper (SR-540) and lock-in amplifier (SR-510) were from Stanford Research systems (Sunnyvale, Calif., USA). The analog output signal from the lock-in amplifier was read by a plug-in data acquisition card (Star 4.5, Varian), which recorded at 20 Hz followed by the digitalization of the analog signal.

CE system set-up. The CE system was composed of a high voltage power supply and a separation capillary with an effective length of 45 cm (75 um I.D. and 385 um O.D.). The running buffer was 20 mM sodium borate, 10 mM Brij 35® and 2.5% methanol. The capillary was conditioned with 0.1 M sodium hydroxide (NaOH), water and running buffer for 15 minutes each. Between runs, the capillary was reconditioned with 0.1 M NaOH for 4 minutes followed by running buffer for 2 minutes. The running voltage was 12 kV. The injection was done hydrodynamically by raising the capillary inlet by 5 cm for 5 seconds.

In-solution derivatization reaction. The reaction solution was prepared by mixing 10 ul of each amino acid (0.01 mM in water), 10 ul of 1 mg/ml of NBD-F and 60 ul of 10 mM borate buffer at pH 8. This mixture was vortexed for 30 seconds and held in a 60° C. water bath for various periods of time (2, 5, 10, 30 and 60 minutes). The reaction solution was diluted to a final volume of 800 ul with running buffer and stored in an ice bath while waiting to be analyzed.

On-fiber derivatization reaction. A fiber was first cleaned by soaking it in ethanol. It was then dipped into a vial containing NBD-F (2-3 mg/ml in ethanol) for 10 min with magnetic stirring at 1000 rpm. After that it was transferred to a 1-ml Teflon centrifuge tube containing 200 ul of amino acids (0.1 mM) in sodium borate buffer (50 mM, pH 6.0) and dipped in the sample for 20 sec. A 4-ml amber vial containing 1 ml of triethylamine (TEA) was maintained in a 60° C. water bath. The headspace of this vial was basic. When the fiber with extracted analytes was exposed to it, the derivatization reaction took place (15 min).

Whole grape sampling with fiber/CE: interface and off-column desorption. The fiber/CE interface with off-column desorption was described previously. The desorption solvent (2 ul) was placed on the surface of the SPME fiber coating. This small droplet was manually rolled around the surface of the fiber coating. Finally this droplet was placed on top of a section of quartz tubing and it slipped down to the other end of the tubing where the capillary inlet was fixed. The capillary inlet contacted with this droplet for approximately 2 s. Since this quartz tubing was positioned 10 cm above the buffer vials, the droplet was hydrodynamically injected. The capillary electrophoresis was subsequently started. With such an interface, a commercial carbowax/TPR SPME fiber from Supelco could be used.

Fiber/CE interface: on-column desorption. On-column desorption has been described previously for a fiber/CE interface. The SPME micro fibers were made by attaching a 2-cm long silica fiber (100 um diameter) to a 10-cm polyimide coated silica capillary (100 um ID×365 um OD) with epoxy glue. The unit was air-dried overnight. The micro fibers were further etched to approximately 50 um diameter with 50% HF. These fibers were finally housed in stainless steel tubes and were sent to Restek Corporation, Bellefonte, Pa. for coating with carbowax.

Results and Discussion: Separation of amino acid derivatives. The critical micellar concentration (CMC) of Brij 35® is 0.9 mM. The CE running buffer used in these experiments had Brij 35® of 10 mM. Brij 35® not only forms micelles to improve the separation resolution, but also enhances the fluorescence intensity of the amino acid derivatives. Some studies have shown that Brij 35® will enhance the florescence signal of such derivatives by at least three times. The methanol (2.5%) in the running buffer functioned as organic modifier. It helped to increase the solubility of the solutes and enlarged the migration time window. As a result, a better resolution was achieved. Under these conditions, a mixture of five amino acid derivatives (phenylalanine, proline, glycine, glutamate and aspartic acid) was analyzed within 20 minutes.

On-fiber derivatization reaction of amino acids. The on-fiber derivatization of amino acids with NBD-F was first established with fibre/HPLC/fluorescence detector system described. On-fiber derivatization and a CE/LIF detection system has been described in the experimental section. The separation of amino acids derivatives was established. NBD-F reacts with to amines and nucleophiles under a mild basic condition. The peaks observed of sp-a represented the side products of the reaction of NBD-F and TEA. The peaks of sp-b observed are representative of the side products of the reaction of NBD-F with the aqueous buffer components and the sample matrix. NBD-OH is the major side product formed in the reaction of NBD-F with aqueous solution. Glycine could not be analyzed under these conditions because the glycine derivative co-eluted with one of the side-product peaks, sp-b. Glycine has an average migration time of 6.47 min (RSD=1.37%). Using a similar procedure, the fibre/CE/LIF detection system was used for the amino acid analysis. In this study, the fibre/CE with off column desorption was used.

Whole grape sampling:Off-column desorption fibre/CE interface. To demonstrate the application of this technology to the direct analysis of small living objects with on fiber derivatization coupled to a CE/LIF detection system, whole grapes were used as the samples. With a NBD-F doped fiber, the sampling procedure and derivatization reaction took 20 seconds and 20 minutes, respectively. The resulting electropherograms from this method with green grape (G) and red seedless grape (R) illustrate a glutamic derivative found at 7.05 min for the green grape sample and 7.01 min for the red seedless grape sample. These migration times corresponded to the L-glutamate standard 7.04 min. In the fibre/CE experiments, most of the peaks were saturated such that phenylalanine and proline derivatives were hidden in the saturated signal. For further identification of amino acids in the sample, the juice from the grapes was analyzed. The glutamate was also found in the grape juice sample in the form of glutamic acid.

On-column desorption fibre/CE interface. With the off column desorption, fibers with carbowax/TPR coating were used for sampling, while the on-column desorption was used with microfiber having thinner coating. These microfibers had a diameter between 75-50 um, and so could be used to sample smaller living objects. These microfibers were coated with carbowax. Electron microscopy was used to visualize the fibers and the fiber coating was found to be about 10 nm.

The feasibility of using these fibers for the on-fiber labeling reaction coupled to CE/LIF detection system was tested. First, the blank NBD-F solution was extracted with the fiber and desorbed on-column. The doping of NBD-F was successful. After the sampling of amino acid standard and reaction in the TEA headspace, no product was detected.

EXAMPLE 4

Instrument and Method Calibration using Fibers Loaded with Calibration Compound

One of the main advantages of the invention is that it allows very convenient introduction of extracted components onto analytical instrumentation, such as gas chromatography, liquid chromatography, supercritical fluid chromatography, capillary electrophoresis, micro-channel devices and even directly to mass spectrometry and detection instruments. This feature can be further explored for delivering calibration standards to analytical instrumentation. Currently standards are delivered to the instrument by injecting the solvent mixture containing appropriate calibration compounds. However, presence of solvent frequently interferes with calibration procedure. Therefore, it would be to user benefit to eliminate solvents from the calibration procedure. It can be accomplished by desorbing standard loaded fiber into appropriate instrument.

The loading of the fiber can be accomplished by exposing sorbent-coated fiber (extraction phase coated) to the source of the standard. The standard is then adsorbed onto the fiber coating. Another approach is to immobilize chemical standards via chemical reaction onto the fiber, which then is released to the instrument under conditions of increased temperature, light, chemical potential, mobile phase, etc. The second approach ensures stability of the calibrant, but as this Example demonstrates the first approach can also be very effective.

Two calibration methods were used. The first approach used solid sorbent coated fibres. One of the methods is to deliver the calibration compound by utilizing SPME fibre to the analytical instrument. The standard is first extracted from the standard mixture using strong sorbent followed by introduction of the standards loaded fibre into analytical system requiring calibration. In this approach liquid injection is avoided and thus solvent interference to the determination of trace VOC (volatile components) is eliminated. Satisfactory calibration curves were obtained for the very volatile compounds namely methanol, acetone, dichloromethane and chloroform when a 75-um carboxen™/polydimethylsiloxane (CX/PDMS) fiber/coating was used. The standard gases or gas mixtures of VOCs were prepared using the NIST traceable certified permeation tubes combined with gas chambers or by microwave-assisted evaporation. "Stepwise" is the approach to the second calibration method developed during this work for on-site calibration of fibres. In this approach the CX/PDMS coated fibre was loaded with standard followed by exposure to the investigated system and then introduction into GC system for analysis. The accumulation time of analytes can be controlled equal to or different from that of the standard, and the response factors for the analytes can be adjusted accordingly. A good reproducibility of the response factors for BTEX was obtained with the stepwise method. Satisfactory results were obtained by using this method in quantitative analysis of BTEX in the gas station air. The introduction of standard via the stepwise procedure makes the technique more useful in field applications. This approach in some respects resembles standard addition, but also external calibration. It can be used to detect leaks, contaminations and losses from the time of standard loading onto the fibre to introduction to analytical instrument.

Preparation of standard gases or gas mixtures. Up to now several methods have been developed for preparation of standard gas. Two methods were employed in this work to prepare the required standard gases or gas mixtures.

Preparation of gas mixture of BTEX using NIST permeation tubes. The standard gas mixture of BTEX (benzene, toluene, ethylbenzene, p-xylene and o-xylene) was generated with the NIST traceable certified permeation tubes (Kin-Tech Laboratories, La Marque, Tex.) and the gas chambers build in our laboratory. It was a flow-through system with which a constant concentration of standard gas (or gas mixture) can be gained. The temperature was controlled at 50° C. and the air flow rate was at 300 ml/min. The gas mixture was sampled from the gas chamber.

Microwave-assisted generation of gas standards of VOCs. A domestic microwave oven (1000W, Model MW5490W, Samsung, Korea) and 1-L gas sampling bulbs (Supelco, Bellefonte, Pa.) were used for preparation of standard gases and gas mixtures of the investigated VOCs with different concentrations. The inner walls of glass bulbs were deactivated by silanization and the bulbs were cleaned with flushing nitrogen before use. For preparation of standard gases or gas mixtures of BTEX, 1,3-dichlorobenzene, 1,1, 2-trichloroethane and tetrachloroethylene, a clean piece of glass wool (ca. 10 mg) was set inside the sampling port of the bulb each time and was moistened with deionized water (15 µL). Water was used to absorb microwave energy and then to prompt the evaporation of the compounds that are poor absorbers of microwave. For preparation of standard gas mixtures of acetone, methanol, dichloromethane and chloroform, no glass wool and water were needed. The port of the glass bulb was sealed with a Teflon-faced silicon rubber septum through which a certain volume of liquid of target compound (or mixture of several compounds) was injected onto the glass wool. Finally, the bulb was placed into the microwave oven to receive microwave radiation for 90 s. The microwave output was always set to the maximum power level. After cooling the Supelco bulb to room temperature, analysis of the standard gas was performed through the sampling port of the bulb where a septum is located.

The device and the "stepwise" procedure. Fiber coatings and conventional samplers used were provided by Supelco (Bellefonte, Pa.). The coatings utilized included 75-μm Carboxen™/Polydimethylsiloxane (CX/PDMS), 85-μm Polyacrylate (PA), 100-μm Polydimethylsiloxane (PDMS) and 65-μm polydimethylsiloxane/divinylbenzene (PDMS/DVB).

The stepwise procedure was conducted as follows: first, the fiber was exposed to tetrachloroethylene standard gas in the bulb, then the fiber was withdrawn into the needle after 2-min extraction and a Thermogreen Septum (LB-2, Supelco) was used to seal the tip of the needle. When using the field SPME sampler, no separate sealing septum is needed. The tetrachloroethylene loaded fiber was then exposed to BTEX standard gas mixture in the chamber or to real air sample for a few minutes. Finally, the fiber was transferred to the GC injector to desorb the standard and analytes at the same time.

GC-FID analysis of analytes. A Varian model 3500 GC equipped with a flame ionization detector (FID) was employed for sample analysis. A SPB-5 capillary column (30 m×0.25 mm×1 μm) from Supelco (Bellefonte, Pa.) was used and hydrogen as carrier gas at 30 psi. The column was programmed as follows: 35° C. initial, held for 1 min, ramp to 135° C. at 10° C./min and held for 1 min. The detector was maintained at 280° C. For the PA, PDMS and PDMS/DVB fibers, the injector was controlled at 250° C. and desorption time was 1 min, while CX/PDMS fiber was desorbed for 2 min at 300° C.

Comparison of introduction of VOCs standards into GC system by syringe injection of standard solution and by standards-loaded fiber. Several very volatile compounds, namely acetone, chloroform, dichloromethane and methanol, were selected for investigation. A standard solution was prepared using methanol as the solvent and the concentration of acetone, dichloromethane and chloroform was 10 μg/ml for each compound. The GC-FID chromatogram obtained by injecting 0.1 μl of the standard solution into the GC system illustrated that the solvent peak was too large to be well separated from peaks of other compounds and thus made it difficult to accurately determine those trace components.

On a contrary, there was no big solvent peak appearing in the chromatograms obtained by injecting a standards-loaded fiber into the GC system and an ideal separation and identification of the VOCs were therefore achieved. The analysis of the standard gas mixture was conducted for 3 min using a 75-μm CX/PDMS fiber and the concentration of acetone, chloroform, dichloromethane and methanol in the standard gas mixture was 50.5 μg/L for each compound. Due to the avoidance of solvent injection, it became easy to get satisfactory chromatograms for the micro amount of VOC standards, even for the very volatile compounds that possess quite short retention times.

In addition, it is difficult to obtain a calibration curve by directly injecting pure liquid of individual VOC or liquid mixture of VOCs into GC system to avoid introduction of plenty of solvent due to the difficulty of accurate injection of a very small volume (<<0.1 μl) of liquid standards into the GC system to match the quantitative ranges of trace analysis.

Calibration curves obtained with this technique for GC analysis of some VOCs. Two different fibers were used to extract the standard gas mixtures of two different groups of VOCs. The very volatile compounds, including acetone, chloroform, dichloromethane and methanol, were extracted with a 75-μm CX/PDMS fiber, which has a high affinity towards to VOCs as described above. BTEX were extracted with a 100-μm PDMS fiber. It is known that the PDMS fiber extract target compounds by absorption while CX/PDMS fiber works by adsorption. By introduction of the VOCs standards into GC system with fibers, satisfactory calibration curves regarding the concentration-response relationship for SPME-GC-FID analysis of the mentioned VOCs were obtained and shown in FIG. 2. The related calibration equations were listed below:

Methanol: $A = 767.69C + 3564$, $R^2 = 0.9937$ (1-a)

Acetone: $A = 3234.8C + 22693$, $R^2 = 0.9952$ (1-b)

Dichloromethane: $A = 1004.6C + 7271.5$, $R^2 = 0.9965$ (1-c)

Chloroform: $A = 980.46C + 719.5$, $R^2 = 0.9993$ (1-d)

Benzene: $A = 106.18C - 1069.5$, $R^2 = 0.995$ (2-a)

Toluene: $A = 326.42C - 4320.8$, $R^2 = 0.9993$ (2-b)

Ethylbenzene: $A = 711.53C - 6136.8$, $R^2 = 0.9958$ (2-c)

p-Xylene: $A = 868.43C - 10704$, $R^2 = 0.9994$ (2-d)

o-Xylene: $A = 995.98C - 9588.1$, $R^2 = 0.9972$ (2-e)

where A is the chromatographic peak area (counts) and C is the concentration of VOCs standard gas (μg/L).

The experimental results demonstrated that the investigated fibers are efficient for introducing VOCs standards into GC system without solvent injection for getting calibration curves and fibre-GC is a highly feasible method for quantitative analysis of VOCs, even for the very volatile compounds.

Moreover, it is also possible to establish the "mass:response" calibration curves for GC analysis of VOCs by introducing standards with SPME fibers. When absorption-type fibres are employed to extract analytes, there is a direct relationship between the initial analyte concentration in the sample ($C_0$) and the amount of the analyte extracted by the fibre at equilibrium (n) according to Equation 3-a:

$$n = \frac{K_{fs} V_s V_f C_0}{V_s + K_{fs} V_f} \quad (3\text{-}a)$$

where $K_{fs}$ is the fibre/sample partition coefficient, $V_f$ is the fibre coating volume and $V_s$ the sample volume. For adsorption-type SPME process, the amount of analyte A extracted by the fibre at equilibrium (n) also grows with the increase of the initial analyte concentration in the sample ($C_{0A}$) before saturated adsorption reached:

$$n = C_{fA}^\infty = \frac{K_A C_{0A} V_s V_f (C_{f\max} - C_{fA}^\infty)}{V_s + K_A V_f (C_{f\max} - C_{fA}^\infty)} \quad (3\text{-}b)$$

where $K_A$ is the adsorption equilibrium constant of analyte A, $C_{fA}$ is the concentration of analyte A on the fibre at steady state, $C_{f\max}$ is the concentration of active sites on the surface (corresponding to the maximum achievable analyte concentration on the surface), $V_s$ and $V_f$ are the volumes of the sample and the fibre coating, respectively.

Stability of VOCs on extraction phase coatings after exposing the coatings to zero air. Analytes present in sample by either absorption or adsorption, collect or enrich the target compounds from samples onto the coatings. However, similar to other extraction procedures, enrichment is followed by an opposite procedure, the release of extracted compounds from the coating phase. Therefore, when a coating loaded with some VOCs is exposed to pure air, a part of extracts will transfer to the air and then the extracts tend to reach an equilibrium distribution between the coating and air phases. The release of the extracts from the coating phase depends on a lot of factors, mainly the compounds' and coatings' properties, the temperature of the environment and the differences of the compounds' concentrations in the coating phase and in the sample or environment. It was shown in Table 2 that the remains of several VOCs (BTEX were included) on the 85-μm PA, 100-μm PDMS and 65-μm PDMS/DVB coatings ranged from 0 to 91.5% after exposing the coatings to zero air for 1 min at room temperature. However, the 75-μm CX/PDMS coating could store the extracts as much as 89.9%-97.2% even through a 6-min exposure to zero air under the same conditions. Actually, no obvious losses could be found for most of the extracts on the 75-μm CX/PDMS coating when exposure time was controlled within 4 min. Thus it is possible to allow a "stepwise" procedure conducted with the CX/PDMS coating-that is, this coating can be used to extract a compound in first step and then transferred to extract other compounds while the compound extracted previously still remains on the coating.

Selection of internal standard for BTEX analysis with stepwise Procedure. 1,3-dichlorobenzene, 1,1,2-trichloroethane and tetrachloroethylene were tested, respectively, as internal standards for BTEX analysis when a 75-μm CX/PDMS coating was used. The CX/PDMS coating has a strong affinity towards these compounds and their storage on the CX/PDMS coating was close to that of BTEX. Considering their chromatographic behaviors, tetrachloroethylene is the best internal standard for BTEX analysis since it can be well separated from BTEX and its peak is located in the central position of the chromatogram. Further investigation demonstrated that, under the selected conditions, the loading of tetrachloroethylene on the fiber did not affect the BTEX, and in turn, the BTEX did not affect the storage of tetrachloroethylene on the fiber either. Tetrachloroethylene as the internal standard for BTEX analysis has another advantage that is, its background is generally not present in main BTEX sources like petroleum. However, tetrachloroethylene also has its drawbacks: it is a halogenated compound and the GC-FID response for it is not as sensitive as for BTEX. The problem involved in determination sensitivity for tetrachloroethylene can be solved by using selective detectors like MSD or FPD.

Response factors for BTEX when tetrachloroethylene was used as internal standard. For chromatographic analysis, the response factor (F) can be defined as the following form:

$$\frac{Ax}{Cx} = F\frac{As}{Cs}, \quad (4)$$

where Ax and As are the peak areas of analyte X and internal standard, while Cx and Cs the concentrations of analyte X and standard after they have been mixed together. For the use of tetrachloroethylene as internal standard for BTEX analysis following the stepwise procedure described above, the standard is not mixed with analytes before they were extracted onto the SPME fiber. In such a case Cs stands for tetrachloroethylene's concentration of the standard gas and Cx is individual BTEX's concentration in the sample.

For the stepwise GC/FID analysis of BTEX, the response factors were measured. The time for of BTEX was 2 min, equal to that for the standard. It can be seen that the response factors highly coincided for duplicate tests in almost all cases. This reflects that the stepwise procedure is a feasible and practicable method to introduce internal standard for GC analysis of BTEX when the CX/PDMS coating is used.

Effect of extraction time on response factors for stepwise procedure. It should be noticed that the response factors discussed above are not only related to the sensitivity of GC-FID determination to individual BTEX but also depend on the SPME efficiency for them. Since the standard and BTEX were not extracted at the same time during the stepwise procedure, the time for BTEX can be controlled equal to or different from that for the standard. Obviously, time control will significantly affect the response factors. This is one of special features of the stepwise procedure distinguishing with the conventional way to use internal standards. In the conventional way, the extraction of analytes and internal standard is conducted simultaneously. It was found that the response factors varied linearly with the time for SPME of BTEX in the range of 1-5 min when SPME time for tetrachloroethylene (standard) was constantly controlled as 2 min. The linear equations obtained were as follows:

Benzene: $F=4.265t+1.301$, $R^2=0.9979$; (5-a)

Toluene: $F=5.776t+0.402$, $R^2=0.9981$; (5-b)

Ethylbenzene: $F=4.663t-0.031$, $R^2=0.9996$; (5-c)

p-Xylene: $F=4.623t-0.247$, $R^2=0.9993$; (5-d)

o-Xylene: $F=4.767t-0.703$, $R^2=0.9963$, (5-e)

where F is response factor and t is time in minute for BTEX.

The concentrations of both standard and analytes were within the linear ranges when the internal standard was used. GC-FID is known to have a linear response to VOCs during a very wide range and so is the inventive procedure with the CX/PDMS coating. The excellent linearity of the response factors for BTEX varying with the extraction time also reflected that the compounds' concentrations studied were located within the linear range.

Field application—analysis of BTEX in the air of a gas station. The VOCs (BTEX were the interests) were sampled from a gas station that is 5-min walk to our laboratory, using the home-made field sampler with a 75-μm CX/PDMS coating. It was a clear day and the temperature was ca. 24° C. when the sampling was conducted. The glass bulb holding the standard gas of tetrachloroethylene (8.1 μg/L) was carried to the field and analysis of tetrachloroethylene was performed prior to BTEX. The sampling time was 2 minutes for the standard and 4 minutes for the gas station air. As soon as the sampling was finished, the sampler was delivered to the laboratory and then the fiber was immediately introduced to GC-FID. The identification of individual BTEX was based on their retention times as well as GC-MS analysis using a Hewlett-Packard 6890 GC equipped with a 5973 MSD (Agilent Tech., USA). Tetrachloroethylene was not found in the gas station air itself. The separation of standard and BTEX from other components of the extracts was very good, only one peak might contain m- and p-xylenes, which couldn't be separated from each other under the selected chromatographic conditions. Finally, using the peak areas obtained (As and Ax), the standard concentration (Cs) and the response factors (F) given by Equations 5-a-5-e, the concentrations of BTEX in the air were calculated according to Equation 4.

Conclusion. For getting calibration curves in GC analysis of VOCs in air, fiber was successfully used to introduce VOCs standards into GC system without solvent injection. The avoidance of solvent injection with the inventive technique made it easy to obtain satisfactory chromatograms for micro amount of VOC standards, even for the very volatile compounds that possess quite short retention times. Moreover, a stepwise method was developed to introduce internal standard for GC analysis of BTEX in field application. The CX/PDMS was proved to be the only suitable coating to fit this method due to its extraordinary affinity towards VOCs. Tetrachloroethylene was selected as the internal standard for reasons such as its proper retention time compared with those of BTEX for GC analysis, similar behaviors to BTEX on the CX/PDMS coating and very low background in main BTEX contamination sources in the environments. Using the developed method, analytical results can be calibrated without a necessity to spike standard material into samples, hence it makes the inventive procedure even more advantageous in field applications. However, since the standard is not directly added into the sample and the analysis of standard and analytes is conducted stepwise, this method may not meet the need of calibration of the air matrix's effects on the analysis of BTEX. This approach is also suitable to detected problems with fiber storage in filed devices, such as leaks, which will result in analyte and standard losses. Further development of the technology can include chemical immobilization of compounds, which will facilitate production of certified standards.

EXAMPLE 5

Electrophoresis in Non-Uniform Channel Modulated by Insert

Electrophoretic behavior of analyte in capillary consisted of two parts with different cross-section was investigated. The modulation of the separation path was achieved by inserting into the capillary a cylindrical fiber at different depth. The sample loaded at the end of lower cross-section and the appropriate zone, at it was demonstrated, spatially narrowed in the wide capillary part according to the electric field strength ratio in the two parts of the capillary. Additionally, the low conductive sample buffer can enhance the further signal narrowness and increase the total probe amount, introduced into the capillary by electroinjection. The applications of this concentration technique includes focusing after desorption from SPME fibers into the electrophoretic separation channel prior separation or prior to direct detection using for example UV-Visible, Fluorescence, electrochemical, NMR or mass spectrometry detection. Also, focusing of analytes present in a buffer is possible by inserting different shapes inserts prior to separation or direct detection. Periodic insertion of the insert into the channel will modulate the concentration of analyte, which facilitate separation and monitoring of the system connected to the separation channel. The modulation input could be random and the signal can be then analyzed by multiplex data processing techniques, such as cross-correlation. Modulation of the diameter of the channel can be also accomplished by applying external pressure or electrical pulses, which will also result in focusing without need for movement of the insert in and out of the channel. The results described below indicate that the focusing occur in a cross channel configuration since the channel cross-section diameter increasing substantially in the area where two channels meet. This can be used effectively to facilitate concentration of analyte prior to separation in the second channel, or in two-dimensional separation when the separation in the first channel is followed by focusing at the interface between the two channels prior to second dimension separation in the second channel.

Introduction. Non-constant form of a separation channel in electrophoresis is a way of providing the variance of some parameters (electric field strength, temperature, pH) which can play an important role for the process concerned. Smooth form changing is required should one need to obtain the appropriate smooth function. By varying a cross-section of electrophoretic camera one obtains an electric field gradient, this gradient can be used both in combination with some other force applied, what is used in so-called "gradient focusing techniques" or by itself provided the current density drop and the chamber design are appropriate to form sufficient temperature difference. The latter effect was used in IEF in thermogradients caused by internal Joule heating.

A separation channel, composed of few different parts but each one of constant form, can be used rather for sample introducing, detecting, multi step analysis development in microarray etc. The results described in this paper are also important for the methodologies where the sample application procedure is connected with a long object inserting (e.g. microfiber) into the separation capillary.

Experimental: Apparatus. The whole-column imaging detection (WCID) of UV absorbance was conducted in the iCE280 CIEF instrument (Convergent Bioscience Ltd., Toronto, Canada) with a fixed wavelength of 280 nm. A short fused-silica capillary (5.5 cm long) with an ID. of 100 um, internally coated with fluorocarbon (J&W Scientific, Folsom, Calif.), was assembled in a cartridge format (Convergent Bioscience Ltd.) The entire process of capillary conditioning, sample injection, data collection, and processing was implemented by a PC computer, and the electropherogram was recorded as absorbance versus the distance to the anode.

Materials and Chemicals. Optical fiber with a 50 and 61.5 um core (FHP050055065 & FVP60072082) was purchased from Polymicro Technologies Inc.(Phoenix, Ariz.). pI-markers and buffer chemicals were obtained from Bio-Rad. Water was purified using an ultrapure water system (Barnstead/Thermolyne, Dubuque, Iowa) and was used for all solutions.

Procedures. The fiber was inserted into the capillary at different distances and the capillary was filled with running buffer (Phosphate 5-100 mM, BioRad). Then, the sample was injected electokinetically, with the injection time being specially selected to achieve complete replenish of the first the first capillary part (containing an inserted microfiber). After, the electrode reservoirs were washed and the desired buffer was placed and the electrophoretic run performed.

Results and Discussion. The initial zone width is an important matter in CZE. For the case the sample concentration is insufficient to provide sensitive detection, a number of on-line preconcentration procedures is developed. The simplest electrophoresis-based techniques are connected with a special conductivity profile creation allowing us to achieve a higher electric field strength value in the sample zone place, although concentration mechanism may be different (e.g., CE- or ITF-based). The similar effect of electric field enhancing can be obtained due to stepwise cross-section change.

In these experiments, by inserting the cylindrical microfiber the cross-section of the separation channel was modulated. Sample was injected electrokinetically at 500 v, the duration of voltage pulse was controlled to achieve complete filling of the first part of the capillary (up to the end of microfiber).

The initial starting zone was rather wide (taking into account the "dead" volume-around one half of the capillary). Then it was effectively compressed, in the same proportion as one could expect starting from cross section difference. In the case of two co-axial cylinders the cross-section ratio (R=S2/S1) is: R=D2/(D2−d2), where D is the diameter of the capillary and d is the one of the microfiber inserted. By the assumptions of constant conductivity, the electric field increase in the narrow part (E1/E2) is defined by S2/S1, and the initial zone length should be narrowed in the same proportion, approximately.

The effect of observed can be combined with methods traditionally used for sample preconcentration. With using low conductivity buffer it was possible to achieve an essential concentration sample increase in the plug introduced, although the peak width change was less evident.

This effect described above does not provide by itself any concentration increase in the introduced probe, since the volume of the sample zone should remain constant and the sample plug narrowing is due to it form change. But this simple and clearly visible effect still opens a lot of important applications to start with to start the separation from "initially wide" zone when it is necessary. For example, working with the inventive technique, one can insert a microfiber into the capillary and obtain a rather wide starting zone, with electric field application the initial zone can effectively be narrowed at the end of microfiber. The latter effect, obviously, depends on the relative size of microfiber inserted, and to achieve high zone narrowing the (D-d) difference should be small enough.

Solid phase microextraction and direct desorption of fluorescent labelled analytes into the separation channel was observed. The process is monitored by the fluorescence whole column imaging detection. The excitation light is delivered to the separation channel using the fiber. This work successfully demonstrates the stacking process that occurs in CE coupling interface with LIF imaging detection. Based on the enhancement in fluorescence intensity, concentration efficiency can be approximated to be as high as a 10-fold. Higher concentration efficiency could be expected with further optimization of configuration of the interface and the experimental conditions used, such as, dimensions of separation capillary and fibre, buffer concentration and applied voltage. The stacking effect generated by such an interface is beneficial to separation efficiency and detection sensitivity of CE separation.

The above-described embodiments of the present invention are intended to be examples only. Alterations, modifications and variations may be effected to the particular embodiments by those of skill in the art without departing from the scope of the invention, which is defined solely by the claims appended hereto.

The invention claimed is:

1. A solid phase microextraction sampling device for collecting a component from an animal or animal tissue, said sampling device comprising:
at least one fibre consisting of a coated end which is at least partially coated with a polymeric extraction phase for extracting said component; and
a positioning device for guiding said coated end into position within a blood vessel of the animal or animal tissue, said positioning device comprising:
a catheter for placement within the blood vessel, through which said fibre extends, said catheter having an open end for positioning within the blood vessel, and said catheter being immobilized during sampling with respect to the blood vessel; and
a fibre holding region attached to the end of the fibre opposite to the coated end of the fibre, said fibre holding region being movable with respect to the catheter, to move said coated end of the fibre into or out of the blood vessel;
wherein said fibre is a flexible wire; and
wherein said extraction phase is loaded with a calibrant prior to sampling.

2. The sampling device of claim 1, wherein the coated end of said fibre is further coated with a polymeric biocompatible protection layer.

3. The sampling device of claim 2, wherein said biocompatible protection layer comprises polypyrrole or derivatised cellulose.

4. The sampling device of claim 1, wherein said extraction phase is a matrix for a MALDI-TOFMS analysis.

5. The sampling device of claim 1, wherein said extraction phase contains a fluorescent label or an enzyme.

6. The sampling device of claim 1, further comprising an openable housing for said fibre.

7. The sampling device of claim 1, comprising a plurality of said fibres capable of being simultaneously positioned in separate locations in said animal or animal tissue.

8. The sampling device of claim 1, additionally comprising a needle in which said fibre is housed, said needle being insertable into said catheter.

9. The sampling device of claim 1, comprising a plurality of said fibres for positioning at the same location in said animal or animal tissue.

10. The sampling device of claim 1, wherein said extraction phase comprises substituted or unsubstituted poly (dimethylsiloxane), polyacrylate, poly (ethylene glycol), carbon, poly(divinylbenzene) or polypyrrole.

11. The sampling device of claim 1, wherein said polymeric extraction phase additionally comprises a bioaffinity agent selected from the group consisting of a selective cavity, a molecular recognition moiety, a molecularly imprinted polymer and an immobilized antibody.

12. A solid phase microextraction sampling device for collecting a component from an animal or animal tissue, said sampling device comprising:
at least one fibre consisting of a coated end which is at least partially coated with a polymeric extraction phase for extracting said component; and
a positioning device for guiding said coated end into position within a blood vessel of the animal or animal tissue;
wherein said extraction phase is loaded with a calibrant prior to sampling.

13. The sampling device of claim 12, wherein the coated end of said fibre is further coated with a polymeric biocompatible protection layer.

14. The sampling device of claim 13, wherein said biocompatible protection layer comprises polypyrrole or derivatised cellulose.

15. The sampling device of claim 12, wherein said extraction phase is a matrix for a MALDI-TOFMS analysis.

16. The sampling device of claim 12, wherein said extraction phase contains a fluorescent label or an enzyme.

17. The sampling device of claim 12, further comprising an openable housing for said fibre.

18. The sampling device of claim 12, comprising a plurality of said fibres capable of being simultaneously positioned in separate locations in said animal or animal tissue.

19. The sampling device of claim 12, comprising a plurality of said fibres for positioning at the same location in said animal or animal tissue.

20. The sampling device of claim 12, wherein said extraction phase comprises substituted or unsubstituted poly (dimethylsiloxane), polyacrylate, poly (ethylene glycol), carbon, poly(divinylbenzene) or polypyrrole.

21. The sampling device of claim 12, wherein said polymeric extraction phase additionally comprises a bioaffinity agent selected from the group consisting of a selective cavity, a molecular recognition moiety, a molecularly imprinted polymer and an immobilized antibody.

22. The sampling device of claim 1, wherein the coated end is coated with a polymeric extraction phase.

23. The sampling device of claim 12, wherein the coated end is coated with a polymeric extraction phase.

* * * * *